United States Patent
Jennings et al.

(10) Patent No.: US 11,241,482 B2
(45) Date of Patent: *Feb. 8, 2022

(54) MESENCHYMAL STEM CELL DIFFERENTIATION

(71) Applicants: NOVARTIS AG, Basel (CH); The Scripps Research Institute, La Jolla, CA (US)

(72) Inventors: Lori Jennings, San Diego, CA (US); Kristen Johnson, Santee, CA (US); Peter Schultz, La Jolla, CA (US)

(73) Assignees: NOVARTIS AG, Basel (CH); The Scripps Research Institute, La Jolla, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/723,424

(22) Filed: Dec. 20, 2019

(65) Prior Publication Data

US 2020/0108122 A1  Apr. 9, 2020

Related U.S. Application Data

(60) Continuation of application No. 16/106,893, filed on Aug. 21, 2018, now Pat. No. 10,555,990, which is a continuation of application No. 14/859,126, filed on Sep. 18, 2015, now Pat. No. 10,064,918, which is a division of application No. 13/383,962, filed as application No. PCT/US2010/041850 on Jul. 13, 2010, now Pat. No. 9,139,633.

(60) Provisional application No. 61/225,293, filed on Jul. 14, 2009.

(51) Int. Cl.

| C07K 1/00 | (2006.01) |
|---|---|
| C07K 1/02 | (2006.01) |
| C07K 1/10 | (2006.01) |
| C07K 14/515 | (2006.01) |
| A61K 38/18 | (2006.01) |
| A61K 47/60 | (2017.01) |
| A61K 31/728 | (2006.01) |
| A61K 38/00 | (2006.01) |

(52) U.S. Cl.
CPC ........ *A61K 38/1891* (2013.01); *A61K 31/728* (2013.01); *A61K 47/60* (2017.08); *C07K 14/515* (2013.01); *A61K 38/00* (2013.01)

(58) Field of Classification Search
None
See application file for complete search history.

(56) References Cited

U.S. PATENT DOCUMENTS

| 5,567,440 | A | 10/1996 | Hubbel et al. |
| 5,972,338 | A | 10/1999 | Godowski ............ C07K 14/515 424/185.1 |
| 7,267,819 | B2 | 9/2007 | Ferrara et al. |
| 7,807,464 | B2 | 10/2010 | Zhang et al. |
| 9,139,633 | B2* | 9/2015 | Johnson .................. A61P 19/02 |
| 10,064,918 | B2* | 9/2018 | Jennings .............. A61K 31/728 |
| 10,555,990 | B2* | 2/2020 | Jennings .............. A61K 31/728 |
| 2003/0068627 | A1 | 4/2003 | Rosen et al. |
| 2003/0120056 | A1 | 6/2003 | Goddard ............. A61K 47/642 536/23.5 |
| 2003/0215451 | A1 | 11/2003 | Ferrara ................ C07K 14/515 424/146.1 |
| 2004/0116649 | A1 | 6/2004 | Kozlowski |
| 2005/0054563 | A1 | 3/2005 | Desnoyer et al. |
| 2007/0020757 | A1 | 1/2007 | Zhang et al. |
| 2007/0122881 | A1 | 5/2007 | Surber .................. C12N 15/00 435/69.1 |
| 2007/0134250 | A1 | 6/2007 | Ferrara et al. |
| 2009/0098117 | A1 | 4/2009 | Ferrara et al. |
| 2009/0104210 | A1 | 4/2009 | Tota et al. |
| 2011/0007330 | A1 | 4/2011 | Horner et al. |
| 2011/0097330 | A1 | 4/2011 | Horner et al. |
| 2014/0256643 | A1 | 9/2014 | Johnson et al. |

FOREIGN PATENT DOCUMENTS

| WO | WO 99/055869 | 11/1999 |
| WO | WO 99/58660 | 11/1999 |
| WO | WO 99/67382 | 12/1999 |
| WO | WO 01/05972 | 1/2001 |
| WO | WO 02/083851 | 10/2002 |
| WO | WO2002083851 | 10/2002 |
| WO | WO 03/044172 | 5/2003 |
| WO | WO 06/127809 | 11/2006 |
| WO | WO 08/137641 | 11/2008 |

OTHER PUBLICATIONS

U.S. Appl. No. 16/106,893.
U.S. Appl. No. 14/859,126.
U.S. Appl. No. 13/383,962.
Ono, Mitsuro, et al., "Protein Region Important for Regulation of Lipid Metabolism in Angiopoietin-like 3 (ANGPTL3)", The Journal of Biological Chemistry, 278(43):41804-41809, 2003.
Camenisch, Gieri, et al., "ANGPTL3 Stimulated Endothelial Cell Adhesion and Migration via Integrin alpha v beta 3 and Induces Blood Vessel Formation In Vivo", The Journal of Biological Chemistry, 277(19):17281-17290, 2002.
Valenzuela, David M., et al., "Angiopoietins 3 and 4: Diverging gene counterparts in mice and humans", Proc. Natl. Acad. Sci., 96:1904-1909, 1999.
Angiopoietin-like proteins, Product Flyer, Alexis Biochemicals.
Angiopoietin-like 3 precursor[*Homo sapiens*], NCBI Reference Sequence: NP_055310.1.
Conklin, et al., "Angiopoietin-Related Protein 3 (*Homo sapiens*)". GenBank Direct Submission Accession: AAD34156, Jan. 28, 2000 (retrieved on Jun. 16, 2011), retrieved from the internet http://www.ncbi.nlm.nih.gov/protein/AAD34156, p. 1.

(Continued)

*Primary Examiner* — Maher M Haddad
(74) *Attorney, Agent, or Firm* — Seth E. Cockrum

(57) ABSTRACT

The present invention provides for methods and compositions for treating or preventing arthritis and joint injury.

14 Claims, 9 Drawing Sheets
Specification includes a Sequence Listing.

(56) References Cited

OTHER PUBLICATIONS

Conklin, et al., "Angiopoietin-Related Protein 3 Precursor (Angiopoietin-Like 3)". Uniprot Direct submission Accession: Q9R182 (online). Jun. 15, 2002 (retrieved on Jun. 16, 2011). http://www.uniprot.org/uniprot/Q9R182.txt?version=9, p. 1.

Oike, et al., "Angiopoietin-Related/Angiopoietin-Like Proteins Regulate Angiogenesis", International Journal of Hematology, 2004, pp. 21-28, vol. 80.

Phinney, et al., "Biochemical Heterogeneity of Mesenchymal Stem Cell Populations", Cell Cycle, Dec. 1, 2007, pp. 2884-2889, vol. 6, No. 23, Landes Bioscience.

Hato, et al., "The Role of Angiopoietin-Like Proteins in Angiogenesis and Metabolism", Trends in Cardiovascular Medicine, pp. 6-14, vol. 18, No. 1, Elsevier Science, New York, NY, US.

Chen, et al., "Angiopotietin-like protein 3 cDNA from goat", GenBank Direct Submission ACT67418, Jun. 21, 2009, http://www.ncbi.nlm.nih.gov/protein/ACT67418.1.

Schminke, et al., "Cartilage Repair In Vivo: The Role of Migratory Progenitor Cells", Cur. Rheumatol. Rep, 2014, pp. 1-8; vol. 16, No. 461, Springer.

Khan, et al., "One Flew over the Progenitor's Nest: Migratory Cells Find a Home in Osteoarthritic Cartilage", Cell Stem Cell, Apr. 3, 2009, pp. 282-284, vol. 4, Elsevier Inc.

Valenzuela, et al., "Angiopoietins 3 and 4: Diverging gene counterparts in mice and humans", Proceedings of the National Academy of Sciences of the United States of America, Mar. 2, 1999, pp. 1904-1909; vol. 96, No. 5.

Conklin, et al., "Identification of a Mammalian Angiopoietin-Related Protein Expressed Specifically in Liver", Genomics, Dec. 15, 1999, pp. 477-482, vol. 62, No. 3, Academic Press.

Qvist, et al., "The disease modifying osteoarthritis drug (DMOAD): Is it in the horizon?", Pharmacological Research, 2008, pp. 1-7, vol. 58, Elsevier Ltd.

Gerwin, et al., "The OARSI histopathology initiative—recommendations for histological assessments of osteoarthritis in the rat", Osteoarthritis and Cartilage, 2010, pp. 524-534, vol. 18, Osteoarthritis Research Society International.

Moore, et al., "Fibroblast growth factor-18 stimulates chondrogenesis and cartilage repair in a rat model of injury-induced osteoarthritis", Osteoarthritis and Cartilage, 2005, pp. 623-631, Osteoarthritis Research Society International.

Database Accession No. XP_001501115.1; Jun. 25, 2007; PREDICTED: similar to angiopoietin-related protein 3 [Equus caballus]; http://www.ncbi.nlm.nih.gov/protein/149709517?sat=12&satkey=5358126.

Database Accession NP_01073814.1; Feb. 24, 2008; "angiopoietin-like 3 [Bos taurus]" http://www.ncbi.nlm.nih.gov/protein/122602391?sat=13&satkey=11158563.

Database Accession NP_038941.1, Dec. 30, 2007; angiopoietin-like 3 [Mus musculus]; http://www.ncbi.nlm.nih.gov/protein/33469117?sat=12%satkey=1625442.

Zhang, et al., "Angiopoietin-like proteins stimulate ex vivo expansion of hematopoietic stem cells", Nature Medicine, Feb. 2006; pp. 240-245, vol. 12, No. 2, Nature Publishing Group.

Wilder, et al., "Integrin alpha V beta 3 as a target for treatment of rhematoid arthritis and related rheumatic diseases", Ann Rheum Dis, Nov. 2002, vol. 61, No. 2, 96-99.

Zheng, et al., "Angiopoietin-Like 3 Deficient Bone Marrow has Decreased Ability to Support Hematopoietic Stem Cells", Blood, Nov. 16, 2008, vol. 112, No. 11, pp. 490.

Camenish, et al.; "ANGPTL3 Stimulates Endothelial Cell Adhesion and Migralion via Integrin avb3 and Induces Blood Vessel Formation in Vivo", JBC, May 10, 2002, vol. 277, No. 19, pp. 17281-17290.

Conklin, et al., "Identification of a Mammalian Angiopoietin-Relaled Protein Expressed Specifically in Liver", Genomics, Dec. 15, 1999, pp. 477-482, vol. 62, No. 3, Academic Press.

Schminke, et al., "Cartilage Repair In Vivo: The Role of Migratory Progenitor Cells", Curr. Rheumatol. Rep, 2014, pp. 1-8; vol. 16, No. 461, Springer.

Database Accession NP_01073814.1; Feb. 24, 2008; angiopoietin-like 3 [Bos taurus] http://www.ncbi.nlm.nih.gov/protein/122692391?sat=13&satkey=11158563.

Camenish, et al., "ANGPTL3 Stimulates Endothelial Cell Adhesion and Migration via Integrin avb3 and Induces Blood Blood Vessel Formation in Vivo", JBC, May 10, 2002, vol. 277, No. 19, pp. 17281-17290.

* cited by examiner mANGPTL3 (C terminus)

```
Bovine     1    MYTIKLFLIIAPLVISSRTDQDY[T]LDS[I]SPEPKSRFAMLDDVKILANGLLQLGHGLKDFVHKTKGQINDIFQKLNI
Canine     1    MYTIKLFLFIIPLVISK[K]DRDYSS[Y]DSVSPEPKSRFAMLDDVKILANGLLQLGHGLKDFVHKTKGQINDIFQKLNI
human      1    M[F]TIKLLLFTVPLVISSRIDQDNSSFDS[L]SPEPKSRFAMLDDVKILANGLLQLGHGLKDFVHKTKGQINDIFQKLNI
Mouse      1    MHTIKLFLFVVPLVIASR[V]PDLSSFDSAPSEPKSRFAMLDDVKILANGLLQLGHGLKDFVHKTKGQINDIFQKLNI
consensus        *.****.*....***.*  .**..***************************************************

Bovine     78   FDQSFYDLSLQTNEIKEEEKELRRATSKLQVKNEEVKNMSLEDSKLESLLEEKILLQQKVRYLEDQL[T]LIKNQP
Canine     78   FDQSFYDLSLQTNEIKEEEKELRRTTSKLQVKNEEVKNMSLEINSK[V]ESLLEEKILLQQKVRYLEKQLTSLIKNQP
human      78   FDQSFYDLSLQTSEIKEEEKELRRTTYKLQVKNEEVKNMSLEINSKLESLLEEKILLQQKV[K]LEEQLTNLIQNQP
Mouse      78   FDQSFYDLSLRTNEIKEEEKELRRTSTLQVKNEEVKNMS[V]ELNSKLESLLEEKTALQHKVRALEEQLTNLILSPA
consensus        **********.*.*********.*..*********** *.*********  *..*..* ..

Bovine     154  QIQEYLEVTSLKTLVEQQDNSIKDLLQIVEEQMR[Q]LNQQQSQIKEIENQLRRTGIKESTEISLSSKPRAPRTTPSF
Canine     154  EIQEHPEVTSLKTFVEQQDNSIKDLLQTVEEQMR[Q]LNQQHSQIKEIENQLR-NVIQESTENSLSSKPRAPRTTPFL
human      154  ETPEHPEVTSLKTFVEKQDNSIKDLLQTVQ[D]YK[Q]LNQQHSQIKEIENQLRRTSIQEPTEISLSSKPRAPRTTPFL
Mouse      154  GAQEHPEVTSLK[S]FVEQQDNSIRE[L]LQSVEEQVK[L]SQQHMQIKEIEKQLR[K][T]GIQEH[S]ENSLSSKSRAPRTTPPL
consensus        .. * ****** .**.****...    . **. ******.  ..  ... * ************ .

Bovine     230  HSNETKNVEHDDIPADCTIIYNQGKHTSGIYSIRPSNSQVFNVYCDVKSGSSWTLIQHRIDGSQNFNETWEN
Canine     229  HLNETKNVEHNDIPANCTTIYNRGEHTSGIYSIRPSNSQVFNVYCDVKSGSSWTLIQHRIDGSQNFNETWEN
human      230  QLNE[T]RNVKHDGIPA[E]CTTIYNRGEHTSQ[M]AIRPSNSQVFHVYCDVISGSPWTLIQHRIDGSQNFNETWEN
Mouse      230  QLNETENTEQDD[L]PADQSH[V]NRGEHTSGV[T][K]PRNSQGFNVYCDTQSGSPWTLIQHRKDGSQDFNETWEN
consensus        . **        *** .  ..*.  ***   .*****.*.****  ** .*******.***** ******
```

FIG. 4A

```
Bovine     302  YKYGFGRLDGEFWLGLEKIYSYSIVMQSNYILRIELEDWKD-KYYTEYSFHLGDHETNYTLHLAEISGNGPKAFPEHK
Canine     301  YRYGFGRLDGEFWLGLEKIYSIVKQSNYILRIELEDWDNKHYIEYFFHLGNHETNYTLHLVEITGNILNALPEHK
human      302  YKYGFGRLDGEFWLGLEKIYSIVKQSNVIRIELEDWKDNKHYIEYSFYLGNHETNYTLHLVAITGNVPNAPENK
Mouse      302  YEKGFGRLDGEFWLGLEKIYALVQQSNYILRIELQDWKDSKHVEYSFHLGSHETNYTLHVAEIAGNIPGALPEHT
consensus       *.:************.***.*.****.*:  *.**::****:*********:* .     * *....*:*:

Bovine     377  DIMFSTWDHKAKGHFNCPESNSGGWWYHDVCGENNLNGKYNKPAKAKPERKFQICWKSQDGRLYSIKATKMLIHP
Canine     377  DIVFSTWDHKAKGHVNCPESYSGGWWWHNVCGENNLNGKYNKPQRAKTKPERRRQLVWKSQNGRLYSIKSTKMLIHP
human      378  DIVFSTWDHKAKGHFNCPEGYSGGWWHDECGENNLNGKYNKPRAKSKPERRRQLSWKSQNGRLYSIKSTKMLIHP
Mouse      378  DIMFSTWNHRAKGQLYCPESYSGGWWNDICGENNLNGKYNKPRTKSRPERRRQIYWPQSRKLYAIKSSKMIQP
consensus       **:****:*:**   **. ***** :  **************:  :**::*: ***::*** **:.**::.*

Bovine     453  SDSENSE    459
Canine     453  IDSESSE    459
human      454  TDSESFE    460
Mouse      454  TT-----    455
consensus       :*..:*
```

FIG. 4A (cont.)

```
bovine      1   MYTIKLFLIIAPLVISSRTDQDYIPLDSISPEPKSRFAMLDDVKILANGLLQLGHGLKDFVHKTKGQINDIFQKLNI
equine      1   MYTIKLFLVIAPLVISSRIDQDYSSLDSIPPEPKSRFAMLDDVKILANGLLQLGHGLKDFVHKTKGQINDIFQKLNI
canine      1   MYTIKLFLFIIPLVISSKDRDYSSYDSVSPEPKSRFAMLDDVKILANGLLQLGHGLKDFVHKTKGQINDIFQKLNI
human       1   MTIKLLFIVPLVISSRIDQDNSSFDSLSPEPKSRFAMLDDVKILANGLLQLGHGLKDFVHKTKGQINDIFQKLNI
mouse       1   MHTIKLFLVVPLVIASRVPDLSSEDSAPSEPKSRFAMLDDVKILANGLLQLGHGLKDFVHKTKGQINDIFQKLNI
consensus   1   *.****.*..*..***.*..*...*..*.****************************************** bovine      78  FDQSFYDLSLQTNEIKEEEKELRRATSKLQVKNEEVKNMSLELDSKLESLLEEKILLQQKVRYLEDLTDLIKNQP
equine      78  FDQSFYALSLQTNEIKEEEKELRRTTSKLQVKNEEVKNMSLELNSKLESLLEEKSLQQKVKYLEEQLTKLIKNQP
canine      78  FDQSFYDLSLQTNEIKEEEKELRRTTSKLQVKNEEVKNMSLELNSKVESLLEEKILLQQKVRYLEKQLTSLIKNQP
human       78  FDQSFYDLSLQTSEIKEEEKELRRTTYKLQVKNEEVKNMSLELNSKLESLLEEKILLQQKVKYLEEQLTNLIQNQP
mouse       78  FDQSFYDLSLRTNEIKEEEKELRRTTSTLQVKNEEVKNMSVELNSKLESLLEEKTALQHKVRALEEQLTNLILSPA
consensus   81  ******.***.*.***********.**.****************.** *******.**..*.**..**

bovine      154 QIQEYLEVTSLKTLVEEQQDNSIKDLLQIVEEQYRQLNQQQSQIKEIENQLRRTGIKESTEISLSSKPRAPRTTPSF
equine      154 EIQEHPEVTSLKTFVEEQQDNSIKDLLQTMEEQYRQLNQQHSQIKEIENQLRRTGIQESTENSLSSKPRAPRTTPSF
canine      154 EIQEHPEVTSLKTFVEEQQDNSIKDLLQTVEEQYRQLNQQHSQIKEIENQLR-NVIQESTENSLSSKPRAPRTTPFL
human       154 ETPEHPEVTSLKTFVEKQDNSIKDLLQTVEDPYPLNQQHSQIKEIENQLRRTSIQEPTEISLSSKPRAPRTTPFL
mouse       154 GAQEHPEVTSLKSFVEEQQDNSIRELLQSVEEQYKLSQQHMQIKEIEKQLRKTGIQEPENSLSSKSRAPRTTPPL
consensus   161 ...*..***.....*****..*.....*.....*...*...**.*.*.********** bovine      230 HSNETKNVEHDDIPADCTIIYNQGKHTSGIYSIRPSNSQVFNVYCDVKSGSSWTLIQHRIDGSQNFNETWEN
equine      230 HLNETKDVEHDDFPADCTTIYNRGEHTSGIYSIPSNSQVFNVYCDVISGSSWLIQRRIDGSQNFNETWQN
canine      229 HLNETKNVEHNDIPANCTTIYNRGEHTSGIYSIPSNSQVFNVYCDVKSGSSWTLIQHRIDGSQNFNETWEN
human       230 QLNERNVKHDGIPAECTTIYNRGEHTSQMYAIRPSNSQVFHVYCDVISGSPWTLIQHRIDGSQNFNETWEN
mouse       230 QLNETENTEQDDPADSAVNRGEHTSQVTHKPRNSQGFNVYCDTQSGSPWTLIQHRKDGSQDFNETWEN
consensus   241 ..**.....*...****..**.*.*..***.**..********
```

FIG. 4B

```
bovine      302  YKYGFGRLDGEFWLGLEKIYSIVMQSNYILRIELEDWKD-KYYTEYSFHLGDHETNYTLHLAEISGNGPKAFPEHK
equine      302  YKYGFGRLDFEFWLGLEKIYSIVKRSNYILRIELEDWKDNKHTIEYSFHLGNHETNYTLHLVEITGNVPNALPEHK
canine      301  YRYGFGRLDGEFWLGLEKIYSIVKQSNYILRIELEDWNDNKHYIEYFFHLGNHETNYTLHLVEITGNINALPEHK
human       302  YKYGFGRLDGEFWLGLEKIYSIVKQSNYVLRIELEDWKDNKHYIEYSFYLGNHETNYTLHLVAITGNVPNAIPENK
mouse       302  YEKGFGRLDGEFWLGLEKIYSIVQQSNYILRELQDWKDSKHYVEYSFHLGSHETNYTLHVAEIAGNIPGALPEHT
consensus   321  *..********.**********..***..*******..*..**.**.*.**.*******.*.  .* *** .

bovine      377  DIMFSTWDHKAKGHFNCPESNSGGWMYHDVCGENNLNGKYNKPKAKAKPERKEGICWKSQDGRLYSIKATKMLIHP
equine      378  DLVFSTWDHKAKGQLNCLESYSGGWWWHDVCGGDNPNGKYNKPRSKTKPERRRGICWKSQNGRLYLKSTKMLIHP
canine      377  DLVFSTWDHKAKGHVNCPESYSGGWWHINVCGENNLNGKYNKPRAKTKPERRGLYWKSQNGRLYSIKSTKMLIHP
human       378  DLVFSTWDHKAKGHFNCPEGYSGGWWHDECGENNLNGKYNKPRAKSKPERRGLSWKSQNGRLYSIKSTKMLIHP
mouse       378  DLMFSTWNHRAKGQLYCPESYSGGWWNDICGENNLNGKYNKPRTKSRPERRGIYWPQSRKLYAIKSSKMLQP
consensus   401  .**.*.**   .*.*.**... ..*.*****.* *..**** .*.*..**** .* *****.* bovine      453  SDSENSE------  459
equine      454  IDSESFELRQIKKPMN  469
canine      453  IDSESSE-------  459
human       454  IDSESFE-------  460
mouse       454  I-------------  455
consensus   481  .**.* *
```

FIG. 4B (cont.)

MESENCHYMAL STEM CELL DIFFERENTIATION

BACKGROUND OF THE INVENTION

Osteoarthritis (OA) represents the most common musculoskeletal disorder. Approximately 40 million Americans are currently affected and this number is predicted to increase to 60 million within the next twenty years as a result of the aging population and an increase in life expectancy, making it the fourth leading cause of disability. OA is characterized by a slow degenerative breakdown of the joint including both the articular cartilage (containing the cells and matrix which produce lubrication and cushioning for the joint) and the subchondral bone underlying the articular cartilage. Current OA therapies include pain relief with oral NSAIDs or selective cyclooxygenase 2 (COX-2) inhibitors, intra-articular (IA) injection with agents such as corticosteroids and hyaluronan, and surgical approaches.

Mesenchymal stem cells (MSCs) are present in adult articular cartilage and upon isolation can be programmed in vitro to undergo differentiation to chondrocytes and other mesenchymal cell lineages. In part it is regulated by growth factors (TGFβs, BMPs), serum conditions and cell-cell contact.

BRIEF SUMMARY OF THE INVENTION

The present invention provides methods of ameliorating or preventing arthritis or joint injury in a mammal. In some embodiments, the method comprises administering to a joint of the mammal a composition comprising an effective amount of a polypeptide comprising an amino acid sequence having at least 95% identity to SEQ ID NO:1 or 25, thereby ameliorating or preventing arthritis or joint injury in the mammal.

In some embodiments, the individual has arthritis or joint injury. In some embodiments, the individual does not have, but is at risk for, arthritis or joint injury.

In some embodiments, the polypeptide comprises SEQ ID NO:1 or 25.

In some embodiments, the amino acid sequence has at least 95% identity to SEQ ID NOs 2, 3, 4, 26, 27, or 28. In some embodiments, the amino acid sequence comprises SEQ ID NOs: 2, 3, 4, 26, 27, or 28.

In some embodiments, the amino acid sequence is at least 80% identical to any of SEQ ID NOs: 5-24. In some embodiments, the amino acid sequence comprises any of SEQ ID NOs: 5-24.

In some embodiments, the arthritis is selected from the group consisting of osteoarthritis, traumatic arthritis, and autoimmune arthritis.

In some embodiments, the mammal is a human.

In some embodiments, the composition further comprises hyaluronic acid.

The present invention also provides methods of inducing differentiation of mesenchymal stem cells into chondrocytes which form the cartilage matrix. In some embodiments, the method comprises contacting mesenchymal stem cells with a sufficient amount of a polypeptide comprising an amino acid sequence having at least 95% identity to SEQ ID NO:1 or 25 to induce differentiation of the stem cells into chondrocytes.

In some embodiments, the method is performed in vitro. In some embodiments, the method is performed in vivo and the stem cells are present in a mammal. In some embodiments, the mammal is a human.

In some embodiments, the polypeptide comprises SEQ ID NO: 1 or 25.

In some embodiments, the amino acid sequence has at least 95% identity to SEQ ID NOs: 2, 3, 4, 26, 27, or 28. In some embodiments, the amino acid sequence comprises SEQ ID NOs: 2, 3, 4, 26, 27, or 28.

In some embodiments, the amino acid sequence is at least 80% identical to any of SEQ ID NOs: 5-24. In some embodiments, the amino acid sequence comprises any of SEQ ID NOs: 5-24.

The present invention also provides pharmaceutical compositions for intra-articular delivery and systemic delivery. In some embodiments, the composition comprising a pharmaceutically effective amount of a polypeptide comprising an amino acid sequence having at least 95% identity to SEQ ID NO:1 or 25.

In some embodiments, the composition further comprises hyaluronic acid.

In some embodiments, the polypeptide comprises SEQ ID NO:1 or 25.

In some embodiments, the amino acid sequence has at least 95% identity to SEQ ID NOs 2, 3, 4, 26, 27, or 28. In some embodiments, the amino acid sequence comprises SEQ ID NOs: 2, 3, 4, 26, 27, or 28.

In some embodiments, the amino acid sequence is at least 80% identical to any of SEQ ID NOs: 5-24. In some embodiments, the amino acid sequence comprises any of SEQ ID NOs: 5-24.

Additional features, advantages, and embodiments of the invention may be set forth or apparent from consideration of the following detailed description, and claims. Moreover, it is to be understood that both the foregoing summary of the invention and the following detailed description are exemplary and intended to provide further explanation without limiting the scope of the invention as claimed.

Definitions

The terms "peptidomimetic" and "mimetic" refer to a synthetic chemical compound that has substantially the same structural and functional characteristics of a naturally or non-naturally occurring polypeptide (e.g., ANGPTL3). Peptide analogs are commonly used in the pharmaceutical industry as non-peptide drugs with properties analogous to those of the template peptide. These types of non-peptide compound are termed "peptide mimetics" or "peptidomimetics" (Fauchere, J. Adv. Drug Res. 15:29 (1986); Veber and Freidinger TINS p. 392 (1985); and Evans et al. J. Med. Chem. 30:1229 (1987), which are incorporated herein by reference). Peptide mimetics that are structurally similar to therapeutically useful peptides may be used to produce an equivalent or enhanced therapeutic or prophylactic effect. Generally, peptidomimetics are structurally similar to a paradigm polypeptide (i.e., a polypeptide that has a biological or pharmacological activity), such as found in a polypeptide of interest, but have one or more peptide linkages optionally replaced by a linkage selected from the group consisting of, e.g., —CH2NH—, —CH2S—, —CH2-CH2-, —CH=CH— (cis and trans), —COCH2-, —CH(OH) CH2-, and —CH2SO—. The mimetic can be either entirely composed of synthetic, non-natural analogues of amino acids, or, is a chimeric molecule of partly natural peptide amino acids and partly non-natural analogs of amino acids. The mimetic can also incorporate any amount of natural amino acid conservative substitutions as long as such substitutions also do not substantially alter the mimetic's structure and/or activity. For example, a mimetic composition is within the scope of the invention if it is capable of carrying out at least one activity of a polypeptide of interest.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Naturally encoded amino acids are the 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) and pyrrolysine and selenocysteine.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M) (see, e.g., Creighton, *Proteins* (1984)).

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (e.g., a polypeptide of the invention), which does not comprise additions or deletions, for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same sequences. Two sequences are "substantially identical" if two sequences have a specified percentage of amino acid residues or nucleotides that are the same (i.e., 60% identity, optionally 65%, 70%, 75%, 80%, 85%, 90%, or 95% identity over a specified region, or, when not specified, over the entire sequence), when compared and aligned for maximum correspondence over a comparison window, or designated region as measured using one of the following sequence comparison algorithms or by manual alignment and visual inspection. The invention provides polypeptides that are substantially identical to the polypeptides, respectively, exemplified herein (e.g., any of SEQ ID NOs: 1-28), as well as uses thereof including but no limited to use for treating or preventing arthritis or joint injury. Optionally, the identity exists over a region that is at least about 50 nucleotides in length, or more preferably over a region that is 100 to 500 or 1000 or more nucleotides in length, or the entire length of the reference sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman (1970) *Adv. Appl. Math.* 2:482c, by the homology alignment algorithm of Needleman and Wunsch (1970) *J. Mol. Biol.* 48:443, by the search for similarity method of Pearson and Lipman (1988) *Proc. Nat'l. Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., *Current Protocols in Molecular Biology* (1995 supplement)).

Two examples of algorithms that are suitable for determining percent sequence identity and sequence similarity are the BLAST and BLAST 2.0 algorithms, which are described in Altschul et al. (1977) *Nuc. Acids Res.* 25:3389-3402, and Altschul et al. (1990) *J. Mol. Biol.* 215:403-410, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) *Proc. Natl. Acad. Sci. USA* 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) *Proc. Natl. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The term "hyaluronic acid" are used herein to include derivatives of hyaluronic acid that include esters of hyaluronic acid, salts of hyaluronic acid and also includes the term hyaluronan. The designation also includes both low and high molecular weight forms of hyaluronans and cross-linked hyaluronans or hylans. Examples of such hyaluronans are Synvisc™ (Genzyme Corp. Cambridge, Mass.), ORTHOVISC™ (Anika Therapeutics, Woburn, Mass.), and HYALGAN™ (Sanofi-Synthelabo Inc., Malvern, Pa.).

BRIEF DESCRIPTION OF THE DRAWINGS

Characterization of ANGTPL3-induced chondrogenesis.

mANGTPTL3.

Sequence alignment ANGPTL3 sequences. FIG. 4A. Sequence alignment of the human, mouse, bovine, and canine native ANGTPL3 proteins. FIG. 4B. Sequence alignment of the human, mouse, bovine, canine and equine native ANGPTL3 proteins.

In vivo efficacy of mANGTPL3 in a surgical osteoarthritis model. Surgical transection of the anterior cruciate ligament (ACL), medial meniscal tibial ligament (MMTL), and medial collateral ligament (MCL) of the right knee from C57BL/6 mice (n=12/group) was performed to induce instability in the knee joint and thus lead to an OA phenotype. One week following surgery, the mice were dosed intra-articularly as indicated once/per for 3-4 weeks.

DETAILED DESCRIPTION

I. Introduction

Figure 1:
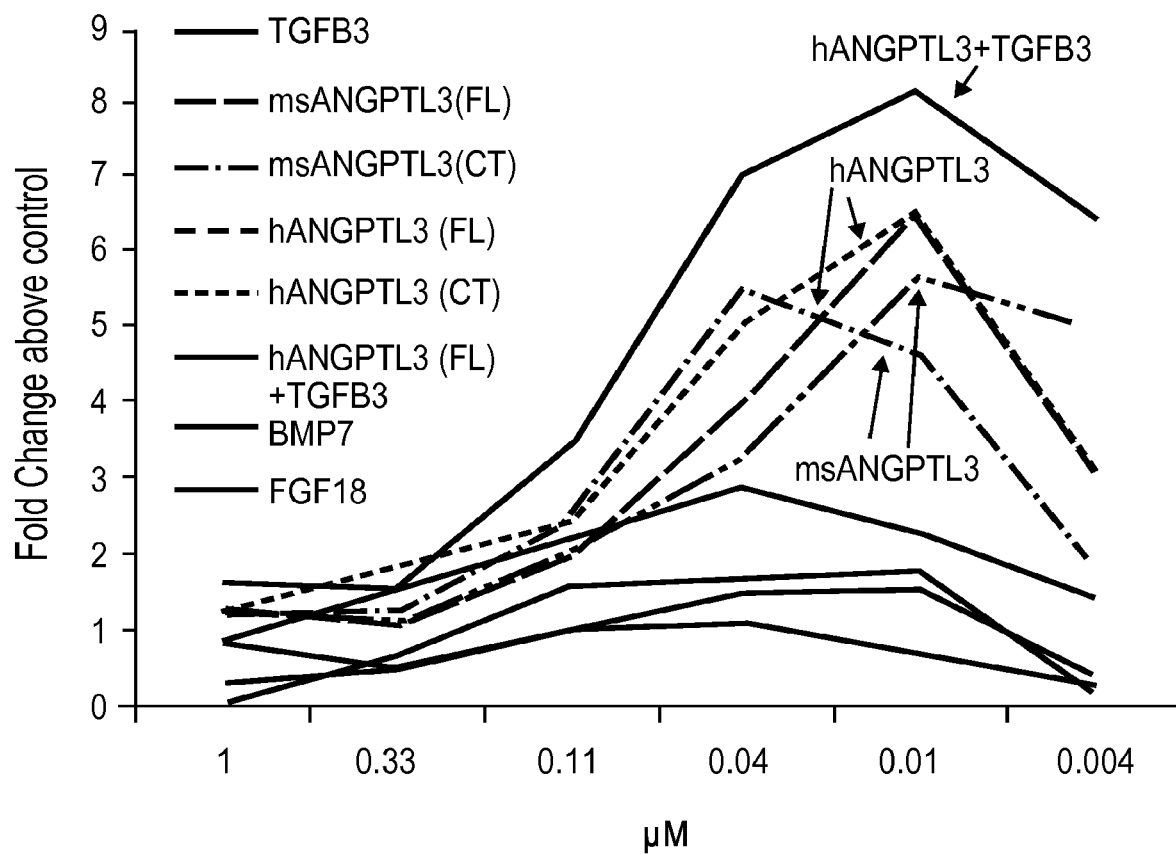
FIG. 1. Quantitative assessment of MSC-induced type II collagen production during in vitro chondrogenesis. hMSCs (10,000/384 well) were plated for 24 hours in hMSC growth media (Millipore). The cells were treated with the proteins above for an additional 72 hours. The media was replaced with serum free DMEM and cultured an additional 14 days in the absence of any additional stimuli. Upon termination, the cells were fixed with formalin, washed, stained with an antibody for type II collagen and counterstained with DAPI. The amount of type II collagen staining was quantitated by high content imaging (Opera, Perkin Elmer). Data is pooled from 3 experiments in duplicate for each dose (n=6).

The present invention is based, in part, on the discovery that Angiopoietin-like 3 (ANGPTL3) stimulates chondrocyte differentiation in mesenchymal stem cells. Accordingly, the present invention provides for methods of induction of mesenchymal stem cell differentiation into chondrocytes. Further, the present invention provides for administration of ANGPTL3 proteins to prevent or ameliorate arthritis or joint injury by administrating an ANGPTL3 protein into a joint, the vertebrae, vertebral disc or systemically.

II. Angiopoietin-Like 3

Angiopoietin-like 3 is a member of the angiopoietin-like family of secreted factors. It is predominantly expressed in the liver, and has the characteristic structure of angiopoietins, consisting of a signal peptide, N-terminal coiled-coil domain (CCD) and the C-terminal fibrinogen (FBN)-like domain. The FBN-like domain in angiopoietin-like 3 was shown to bind $\alpha V/\beta 3$ integrins, and this binding induces endothelial cell adhesion and migration.

A variety of ANGPTL3 proteins can be used according to the present invention. As explained herein, native ANGPTL3 is generally cleaved in vivo into amino-terminal and carboxyl terminal fragments. The present invention contemplates use of various ANGPTL3 proteins having chondrogenic activity. In some embodiments, the invention provides for use of full-length native (or variants thereof) ANGPTL3 protein amino acid sequences. In some embodiments, the invention provides for ANGPTL3 proteins comprising a portion (not the full-length native sequence) of the ANGPTL3 sequence, or a variant thereof, that retains chondrogenic activity, i.e., not the amino-terminal end of the native protein. In some embodiments, the ANGPTL3 proteins of the invention do not have the CCD domain and/or do not have significant CCD activity. Thus, in some embodiments, the ANGPTL3 proteins of the invention comprise at least a fragment (e.g., at least 50, 100, 150, 200, 250 contiguous amino acids) of the native mouse (e.g., SEQ ID NO:12), human (e.g., SEQ ID NO:8), bovine (e.g., SEQ ID NO:16), dog (e.g., SEQ ID NO:20), or equine (e.g. SEQ ID NO:24) ANGPTL3 protein sequence or substantially identical sequences, but do not comprise at least 200 contiguous amino-terminal amino acids of a native ANGPTL3 protein.

In some embodiments, the ANGPTL3 proteins of the invention comprise a fibrinogen-like domain. In some embodiments, the ANGPTL3 proteins of the invention comprise contiguous amino acids corresponding to amino acids 207-455, 207-400, 207-350, 225-455, 225-400, 225-350, 241-455, 241-400, 241-350 of the native mouse (e.g., SEQ ID NO:12), human (e.g., SEQ ID NO:8), bovine (e.g., SEQ ID NO:16), dog (e.g., SEQ ID NO:20), or equine (e.g. SEQ ID NO:24) ANGPTL3 protein sequence or are substantially identical to such sequences, but do not include the flanking native ANGPTL3 protein amino acid sequence. In some embodiments, the ANGPTL3 proteins of the invention (including but not limited to any of SEQ ID NOs: 1-28) but lack at least a portion of the C-terminal sequence, e.g., lack 10, 20, 30, 40, 50 amino acids from the C-terminus.

While the ANGPTL3 proteins of the invention as described above may not include native ANGPTL3 protein sequences flanking the regions described above, the ANGPTL3 proteins of the invention can include non-native ANGPTL3 protein flanking sequences. For example, the chondrogenic active portion of an ANGPTL3 protein can be fused to one or more heterologous amino acids to form a fusion protein. Fusion partner sequences can include, but are not limited to, amino acid tags, non-L (e.g., D-) amino acids or other amino acid mimetics to extend in vivo half-life and/or protease resistance, targeting sequences or other sequences.

The ANGPTL3 proteins of the invention encompass variants and truncations of native ANGPTL3 proteins as well as variants and truncations of active fragments described herein. Active variants can be identified in any number of ways known to those of skill in the art. In some embodiments, amino acid alignments of active proteins can be established to identify those positions that are invariant or that are include conserved amino acid changes. SEQ ID NOs: 1, 2, 3, or 4 represent consensus sequences comprising the invariant amino acids between certain areas (position 241-455, 225-455 and 207-455, and native full-length, respectively) of the human, mouse, bovine, and canine native ANGPTL3 proteins. SEQ ID NOs: 25, 26, 27, or 28 represent consensus sequences comprising the invariant amino acids between certain areas (position 241-455, 225-455 and 207-455, and native full-length, respectively) of the human, mouse, bovine, canine, and equine native ANGPTL3 proteins. Thus, in some embodiments, the chondrogenic ANGPTL3 proteins of the invention comprise SEQ ID NOs: 1, 2, 3, 4, 25, 26, 27, or 28. In some embodiments, the chondrogenic ANGPTL3 proteins of the invention comprise an amino acid sequence substantially identical to any of SEQ ID NOs: 5, 6, 7, 8, 9, 10, 11, 12, 13, 14, 15, 16, 17, 18, 19, 20, 21, 22, 23 or 24 (as measured across the length of SEQ ID NOs).

The ANGPTL3 proteins of the invention have chondrogenic activity. As defined herein, chondrogenesis or chondrogenic activity refers to the development of chondrocytes from MSCs. Indicators of chondrogenic activity include, but are not limited to, cartilage matrix production. Cartilage matrix production may be measured by various markers, for example, such as Sox9, type II collagen, or glycosaminoglycan (GAG) production. In some embodiments, GAG production is measured as a marker for cartilage matrix production. In some embodiments, a 3-fold increase in GAG production with cartilage specific protein expression indicates positive cartilage matrix production.

In some embodiments, the ANGPTL3 polypeptides of the invention will comprise at least one non-naturally encoded amino acid. Methods of making and introducing a non-naturally-occurring amino acid into a protein are known. See, e.g., U.S. Pat. Nos. 7,083,970; and 7,524,647. The general principles for the production of orthogonal translation systems that are suitable for making proteins that comprise one or more desired unnatural amino acid are known in the art, as are the general methods for producing orthogonal translation systems. For example, see International Publication Numbers WO 2002/086075, entitled "METHODS AND COMPOSITION FOR THE PRODUCTION OF ORTHOGONAL tRNA-AMINOACYL-tRNA SYNTHETASE PAIRS;" WO 2002/085923, entitled "IN VIVO INCORPORATION OF UNNATURAL AMINO ACIDS;" WO 2004/094593, entitled "EXPANDING THE EUKARYOTIC GENETIC CODE;" WO 2005/019415, filed Jul. 7, 2004; WO 2005/007870, filed Jul. 7, 2004; WO 2005/007624, filed Jul. 7, 2004; WO 2006/110182, filed Oct. 27, 2005, entitled "ORTHOGONAL TRANSLATION COMPONENTS FOR THE VIVO INCORPORATION OF UNNATURAL AMINO ACIDS" and WO 2007/103490, filed Mar. 7, 2007, entitled "SYSTEMS FOR THE EXPRESSION OF ORTHOGONAL TRANSLATION COMPONENTS IN EUBACTERIAL HOST CELLS." Each of these applications is incorporated herein by reference in its entirety. For discussion of orthogonal translation systems that incorporate unnatural amino acids, and methods for their production and use, see also, Wang and Schultz, (2005) "Expanding the Genetic Code." Angewandte Chemie Int Ed 44: 34-66; Xie and Schultz, (2005) "An Expanding Genetic Code." Methods 36: 227-238; Xie and Schultz, (2005) "Adding Amino Acids to the Genetic Repertoire." Curr Opinion in Chemical Biology 9: 548-554; and Wang, et al., (2006) "Expanding the Genetic Code." Annu Rev Biophys Biomol Struct 35: 225-249; Deiters, et al, (2005) "In vivo incorporation of an alkyne into proteins in *Escherichia coli*." Bioorganic & Medicinal Chemistry Letters 15:1521-1524; Chin, et al., (2002) "Addition of p-Azido-L-phenylalanine to the Genetic Code of *Escherichia coli*." J Am Chem Soc 124: 9026-9027; and International Publication No. WO2006/034332, filed on Sep. 20, 2005, the contents of each of which are incorporated by reference in their entirety. Additional details are found in U.S. Pat. Nos. 7,045,337; 7,083,970; 7,238,510; 7,129,333; 7,262,040; 7,183,082; 7,199,222; and 7,217,809.

A "non-naturally encoded amino acid" refers to an amino acid that is not one of the common amino acids or pyrolysine or selenocysteine. Other terms that may be used synonymously with the term "non-naturally encoded amino acid" are "non-natural amino acid," "unnatural amino acid," "non-naturally-occurring amino acid," and variously hyphenated and non-hyphenated versions thereof. The term "non-naturally encoded amino acid" also includes, but is not limited to, amino acids that occur by modification (e.g. post-translational modifications) of a naturally encoded amino acid (including but not limited to, the 20 common amino acids or pyrrolysine and selenocysteine) but are not themselves naturally incorporated into a growing polypeptide chain by the translation complex. Examples of such non-naturally-occurring amino acids include, but are not limited to, N-acetylglucosaminyl-L-serine, N-acetylglucosaminyl-L-threonine, and O-phosphotyrosine.

A non-naturally encoded amino acid is typically any structure having any substituent side chain other than one used in the twenty natural amino acids. Because the non-naturally encoded amino acids of the invention typically differ from the natural amino acids only in the structure of the side chain, the non-naturally encoded amino acids form amide bonds with other amino acids, including but not limited to, natural or non-naturally encoded, in the same manner in which they are formed in naturally occurring polypeptides. However, the non-naturally encoded amino acids have side chain groups that distinguish them from the natural amino acids. For example, R optionally comprises an alkyl-, aryl-, acyl-, keto-, azido-, hydroxyl-, hydrazine, cyano-, halo-, hydrazide, alkenyl, alkynl, ether, thiol, seleno-, sulfonyl-, borate, boronate, phospho, phosphono, phosphine, heterocyclic, enone, imine, aldehyde, ester, thioacid, hydroxylamine, amino group, or the like or any combination thereof. Other non-naturally occurring amino acids of interest that may be suitable for use in the present invention include, but are not limited to, amino acids comprising a photoactivatable cross-linker, spin-labeled amino acids, fluorescent amino acids, metal binding amino acids, metal-containing amino acids, radioactive amino acids, amino acids with novel functional groups, amino acids that covalently or noncovalently interact with other molecules, photocaged and/or photoisomerizable amino acids, amino acids comprising biotin or a biotin analogue, glycosylated amino acids such as a sugar substituted serine, other carbohydrate modified amino acids, keto-containing amino acids, amino acids comprising polyethylene glycol or polyether, heavy atom substituted amino acids, chemically cleavable and/or photocleavable amino acids, amino acids with an elongated side chains as compared to natural amino acids, including but not limited to, polyethers or long chain hydrocarbons, including but not limited to, greater than about 5 or greater than about 10 carbons, carbon-linked sugar-containing amino acids, redox-active amino acids, amino thioacid containing amino acids, and amino acids comprising one or more toxic moiety.

Exemplary non-naturally encoded amino acids that may be suitable for use in the present invention and that are useful for reactions with water soluble polymers include, but are not limited to, those with carbonyl, aminooxy, hydrazine, hydrazide, semicarbazide, azide and alkyne reactive groups. In some embodiments, non-naturally encoded amino acids comprise a saccharide moiety. Examples of such amino acids include N-acetyl-L-glucosaminyl-L-serine, N-acetyl-L-galactosarninyl-L-serine, N-acetyl-L-glucosaminyl-L-threonine, N-acetyl-L-glucosaminyl-L-asparagine and O-mannosaminyl-L-serine. Examples of such amino acids also include examples where the naturally-occurring N- or O-linkage between the amino acid and the saccharide is replaced by a covalent linkage not commonly found in nature—including but not limited to, an alkene, an oxime, a thioether, an amide and the like. Examples of such amino acids also include saccharides that are not commonly found in naturally-occurring proteins such as 2-deoxy-glucose, 2-deoxygalactose and the like.

Another type of modification that can optionally be introduced into the ANGPTL3 proteins of the invention (e.g. within the polypeptide chain or at either the N- or C-terminal), e.g., to extend in vivo half-life, is PEGylation or incorporation of long-chain polyethylene glycol polymers (PEG). Introduction of PEG or long chain polymers of PEG increases the effective molecular weight of the present polypeptides, for example, to prevent rapid filtration into the urine. In some embodiments, a Lysine residue in the ANGPTL3 sequence is conjugated to PEG directly or through a linker. Such linker can be, for example, a Glu residue or an acyl residue containing a thiol functional group for linkage to the appropriately modified PEG chain. An alternative method for introducing a PEG chain is to first introduce a Cys residue at the C-terminus or at solvent exposed residues such as replacements for Arg or Lys residues. This Cys residue is then site-specifically attached to a PEG chain containing, for example, a maleimide function. Methods for incorporating PEG or long chain polymers of PEG are well known in the art (described, for example, in Veronese, F. M., et al., *Drug Disc. Today* 10: 1451-8 (2005); Greenwald, R. B., et al., *Adv. Drug Deliv. Rev.* 55: 217-50 (2003); Roberts, M. J., et al., *Adv. Drug Deliv. Rev.*, 54: 459-76 (2002)), the contents of which is incorporated herein by reference. Other methods of polymer conjugations known in the art can also be used in the present invention. In some embodiments, poly(2-methacryloyloxyethyl phosphorylcholine) (PMPC) is introduced as a polymer conjugate with the ANGPTL3 proteins of the invention (see, e.g., WO2008/098930; Lewis, et al., *Bioconjug Chem.*, 19: 2144-55 (2008)). In some embodiments, a phosphorylcholine-containing polymer conjugate with the ANGPTL3 proteins can be used in the present invention. A person of skill would readily recognize that other biocompatible polymer conjugates can be utilized.

A more recently reported alternative approach for incorporating PEG or PEG polymers through incorporation of non-natural amino acids (as described above) can be performed with the present polypeptides. This approach utilizes an evolved tRNA/tRNA synthetase pair and is coded in the expression plasmid by the amber suppressor codon (Deiters, A, et al. (2004). *Bio-org. Med. Chem. Lett.* 14, 5743-5). For example, p-azidophenylalanine can be incorporated into the present polypeptides and then reacted with a PEG polymer having an acetylene moiety in the presence of a reducing agent and copper ions to facilitate an organic reaction known as "Huisgen [3+2]cycloaddition."

In certain embodiments, the present invention contemplates specific mutations of the ANGPTL3 proteins so as to alter the glycosylation of the polypeptide. Such mutations may be selected so as to introduce or eliminate one or more glycosylation sites, including but not limited to, O-linked or N-linked glycosylation sites. In certain embodiments, the ANGPTL3 proteins of the present invention have glycosylation sites and patterns unaltered relative to the naturally-occurring ANGPTL3 proteins. In certain embodiments, a variant of ANGPTL3 proteins includes a glycosylation variant wherein the number and/or type of glycosylation sites have been altered relative to the naturally-occurring ANGPTL3 proteins. In certain embodiments, a variant of a polypeptide comprises a greater or a lesser number of N-linked glycosylation sites relative to a native polypeptide. An N-linked glycosylation site is characterized by the sequence: Asn-X-Ser or Asn-X-Thr, wherein the amino acid residue designated as X may be any amino acid residue except proline. The substitution of amino acid residues to create this sequence provides a potential new site for the addition of an N-linked carbohydrate chain. Alternatively, substitutions which eliminate this sequence will remove an existing N-linked carbohydrate chain. In certain embodiments, a rearrangement of N-linked carbohydrate chains is provided, wherein one or more N-linked glycosylation sites (typically those that are naturally occurring) are eliminated and one or more new N-linked sites are created.

Exemplary ANGPTL3 proteins variants include cysteine variants wherein one or more cysteine residues are deleted from or substituted for another amino acid (e.g., serine) relative to the amino acid sequence of the naturally-occurring ANGPTL3 proteins. In certain embodiments, cysteine variants may be useful when ANGPTL3 proteins must be refolded into a biologically active conformation such as after the isolation of insoluble inclusion bodies. In certain embodiments, cysteine variants have fewer cysteine residues than the native polypeptide. In certain embodiments, cysteine variants have an even number of cysteine residues to minimize interactions resulting from unpaired cysteines.

In some embodiments, functional variants or modified forms of the ANGPTL3 proteins include fusion proteins of an ANGPTL3 protein of the invention and one or more fusion domains. Well known examples of fusion domains include, but are not limited to, polyhistidine, Glu-Glu, glutathione S transferase (GST), thioredoxin, protein A, protein G, an immunoglobulin heavy chain constant region (Fc), maltose binding protein (MBP), or human serum albumin. A fusion domain may be selected so as to confer a desired property. For example, some fusion domains are particularly useful for isolation of the fusion proteins by affinity chromatography. For the purpose of affinity purification, relevant matrices for affinity chromatography, such as glutathione-, amylase-, and nickel- or cobalt-conjugated resins are used. Many of such matrices are available in "kit" form, such as the Pharmacia GST purification system and the QIAexpress™ system (Qiagen) useful with (HIS$_6$) fusion partners. As another example, a fusion domain may be selected so as to facilitate detection of the ANGPTL3 proteins. Examples of such detection domains include the various fluorescent proteins (e.g., GFP) as well as "epitope tags," which are usually short peptide sequences for which a specific antibody is available. Well known epitope tags for which specific monoclonal antibodies are readily available include FLAG, influenza virus hemagglutinin (HA), and c-myc tags. In some cases, the fusion domains have a protease cleavage site, such as for Factor Xa or Thrombin, which allows the relevant protease to partially digest the fusion proteins and thereby liberate the recombinant proteins therefrom. The liberated proteins can then be isolated from the fusion domain by subsequent chromatographic separation. In certain embodiments, an ANGPTL3 protein is fused with a domain that stabilizes the ANGPTL3 protein in vivo (a "stabilizer" domain). By "stabilizing" is meant anything that increases serum half life, regardless of whether this is because of decreased destruction, decreased clearance by the kidney, or other pharmacokinetic effect. Fusions with the Fc portion of an immunoglobulin are known to confer desirable pharmacokinetic properties on a wide range of proteins. Likewise, fusions to human serum albumin can confer desirable properties. Other types of fusion domains that may be selected include multimerizing (e.g., dimerizing, tetramerizing) domains and functional domains (that confer an additional biological function, as desired).

III. Angiopoietin-Like 3 Proteins Disease Indications

It is contemplated that the polypeptides, compositions, and methods of the present invention may be used to treat or prevent any type of arthritis or joint injury. It is further contemplated that the polypeptides, compositions, and methods of the present invention may be used to treat or prevent various cartilagenous disorders. In some embodiments, the proteins of the invention are administered to prevent arthritis or joint injury, for example where there is a genetic or family history of arthritis or joint injury or prior or during joint surgery. Exemplary conditions or disorders to be treated or prevented with the polypeptides, compositions, and methods of the invention, include, but are not limited to systemic lupus erythematosis, rheumatoid arthritis, juvenile chronic arthritis, osteoarthritis, degenerative disc disease, spondyloarthropathies, systemic sclerosis (scleroderma), idiopathic inflammatory myopathies (dermatomyositis, polymyositis), Sjogren's syndrome, systemic vasculitis, sarcoidosis, autoimmune hemolytic anemia (immune pancytopenia, paroxysmal nocturnal hemoglobinuria), autoimmune thrombocytopenia (idiopathic thrombocytopenic purpura, immune-mediated thrombocytopenia), thyroiditis (Grave's disease, Hashimoto's thyroiditis, juvenile lymphocytic thyroiditis, atrophic thyroiditis), diabetes mellitus, immune-mediated renal disease (glomerulonephritis, tubulointerstitial nephritis), demyelinating diseases of the central and peripheral nervous systems such as multiple sclerosis, idiopathic demyelinating polyneuropathy or Guillain-Barr syndrome, and chronic inflammatory demyelinating polyneuropathy, hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis, inflammatory bowel disease (ulcerative colitis: Crohn's disease), gluten-sensitive enteropathy, and Whipple's disease, autoimmune or immune-mediated skin diseases including bullous skin diseases, erythema multiforme and contact dermatitis, psoriasis, allergic diseases such as asthma, allergic rhinitis, atopic dermatitis, food hypersensitivity and urticaria, immunologic diseases of the lung such as eosinophilic pneumonias, idiopathic pulmonary fibrosis and hypersensitivity pneumonitis, transplantation associated diseases including graft rejection and graft-versus-host-disease. In some embodiments of the invention, the polypeptides, compositions, and methods of the present invention may be used to treat osteoarthritis.

In some embodiments, the polypeptides, compositions, and methods of the present invention provide a method for stimulating chondrocyte proliferation and cartilage production in cartilagenous tissues that have been damaged due to traumatic injury or chondropathy. Of particular importance for treatment are tissues that exhibit articulated surfaces, such as, spine, shoulder, elbow, wrist, joints of the fingers, hip, knee, ankle, and the joints of the feet. Examples of diseases that may benefit from treatment include osteoarthritis, rheumatoid arthritis, other autoimmune diseases, or osteochondritis dessicans. In addition, cartilage malformation is often seen in forms of dwarfism in humans suggesting that the polypeptides, compositions, and methods would be useful in these patients.

It is contemplated that the polypeptides, compositions, and methods of the present invention may be used to treat a mammal. As used herein a "mammal" to any mammal classified as a mammal, including humans, domestic and farm animals, and zoo, sports or pet animals, such as cattle (e.g. cows), horses, dogs, sheep, pigs, rabbits, goats, cats, etc. In some embodiments of the invention, the mammal is a human.

In some embodiments, the polypeptides of the invention can be heterologous to the mammal to be treated. For example, a bovine ANGPTL3 protein or fragments thereof, a protein or peptide derived from a bovine ANGPTL3 protein (e.g., a modified bovine ANGPTL3 protein, a conservative variant of bovine ANGPTL3 protein, a peptidomimetic derived from a bovine ANGPTL3 protein) are used in the treatment of a human patient. In some embodiments, a heterologous. ANGPTL3 protein can be used to expand chondrocyte populations in culture for transplantation. In some embodiments, the expanded cultures will then be admixed with polypeptides and compositions homologous to the mammal to be treated, and placed in the joint space or directly into the cartilage defect. Alternatively, the polypeptides of the invention are derived from the same species, i.e., a human ANGPTL3 protein or fragments thereof, a protein or peptide derived from a human ANGPTL3 protein (e.g., a modified human ANGPTL3 protein, a conservative variant of human ANGPTL3 protein, a peptidomimetic derived from a human ANGPTL3 protein) is used in the treatment of a human patient. By using a protein derived from the same species of mammal as is being treated, one may avoid inadvertent immune responses.

The polypeptides and compositions of the present invention can be applied by direct injection into the synovial fluid of the joint, systemic administration (oral or intravenously) or directly into the cartilage defect, either alone or complexed with a suitable carrier for extended release of protein. The polypeptides, compositions, and methods of the present invention can also be used to expand chondrocyte populations in culture for autogenous or allogenic chondrocyte transplantation. The transplantation can be optionally administered with concurrent treatment consisting of administration of the polypeptides and compositions of the present invention. In these procedures, for example, chondrocytes can be harvested arthroscopically from an uninjured minor load-bearing area of the damaged joint, and can be cultured in the presence of the polypeptides and compositions of the present invention to increase the number of cells prior to transplantation. The expanded cultures will then be admixed with the polypeptides and compositions of the present invention, and placed in the joint space or directly into the defect. The polypeptides and compositions of the present invention can be used in combination with periosteal or perichondrial grafts that contain cells that can form cartilage and/or help to hold the transplanted chondrocytes or their precursor cells in place. The polypeptides and compositions of the present invention can be used to repair cartilage damage in conjunction with lavage of the joint, stimulation of bone marrow, abrasion arthroplasty, subchondral drilling, or microfracture of the subchondral bone. Additionally, after the growth of cartilage due to the administration of the polypeptides and compositions of the present invention, additional surgical treatment may be necessary to suitably contour the newly formed cartilage surface.

IV. Pharmaceutical Compositions

The dose of a compound of the present invention for treating the above-mentioned diseases or disorders varies depending upon the manner of administration, the age and the body weight of the subject, and the condition of the subject to be treated, and ultimately will be decided by the attending physician or veterinarian. Such an amount of the compound as determined by the attending physician or veterinarian is referred to herein as an "effective amount."

Formulations suitable for administration include excipients, including but not limited to, aqueous and non-aqueous solutions, isotonic sterile solutions, which can contain antioxidants, buffers, bacteriostats, and solutes that render the formulation isotonic, and aqueous and non-aqueous sterile suspensions that can include suspending agents, solubilizers, thickening agents, stabilizers, and preservatives.

The dose administered to a patient, in the context of the present invention should be sufficient to effect a beneficial response in the subject over time. The dose will be determined by the efficacy of the particular protein employed and the condition of the subject, as well as the body weight or surface area of the area to be treated. The size of the dose also will be determined by the existence, nature, and extent of any adverse side-effects that accompany the administration of a particular protein or vector in a particular subject. Administration can be accomplished via single or divided doses.

V. Methods of Administration

Any method for delivering the proteins of the invention to an affected joint can be used. In the practice of this invention, compositions can be administered, for example, intraarticularly (i.e., into a joint), orally, intravenously. The formulations of compounds can be presented in unit-dose or multi-dose sealed containers, such as ampules and vials. Solutions and suspensions can be prepared from sterile powders, granules, and tablets of the kind previously described. The proteins of the present invention can also be used effectively in combination with one or more additional active agents (e.g., hyaluronic acid or a salt thereof) depending on the desired therapy or effect.

EXAMPLES

The following examples are offered to illustrate, but not to limit the claimed invention.

Example 1: High Throughput Screen for Inducers of Chondrogenesis

To identify and define a new, non-invasive strategy for OA joint repair, we developed a non-biased high throughput screen of proteins capable of selectively directing the differentiation of human mesenchymal stem cells (MSCs) to chondrocytes. The assay system models the resident MSCs in cartilage and identifies mediators that stimulate the natural repair potential and enhance integrated cartilage regeneration. We choose to test a unique secreted protein library by a high throughput, cell-based screens of human and mouse MSCs. This approach provides a strategy that allows the rapid identification of uncharacterized and native protein ligands that affect chondrogenesis.

To study these secreted proteins, two approaches were taken: the production of conditioned media (CM) from a mammalian producer cell line (HEK293T) and the generation of purified proteins from free style HEK-F cells. Together these complementary approaches allowed for new target identification in a variety of applications.

Screening of proteins in the MSC assay identified the lead candidate, Angiopoeitin-like 3, abbreviated ANGPTL3. ANGPTL3 was identified in two parallel but orthogonal initial screens of both the CM and purified proteins. In the proof of concept CM screen, C3H10t1/2 cells were incubated for 7 days following transfer of the CM. Chondrogenesis was found to occur in wells containing ANGPTL3-75 assayed by Alcian blue staining for detection of cartilage matrix production. ANGPTL3-75 was independently identified by screening 531 purified proteins for chondrocytic differentiation of human MSCs.

Following the initial screening assays, ANGPTL3 was subsequently characterized in six secondary assays. These assays include: (1) monolayer culture of mouse mesenchymal C3H10t1/2 cells: induction of type II collagen and Sox9 protein expression (markers of chondrogenesis) but no induction of osteocalcin (markers of osteogenesis); (2) inhibition of TNFα/oncostatin M (OSM)—induced nitric oxide (NO) release in bovine chondrocytes; (3) inhibition of TNFα/OSM—induced glycosaminoglycan (GAG) release in bovine cartilage organ culture; (4) induction of cartilage matrix gene expression (aggrecan) in a human MSC pellet culture system; (5) lack of toxicity in primary human chondrocytes, human synovial fibroblasts, and human MSCs; (6) stimulation of proliferation of human chondrocytes.

Figure 2A:
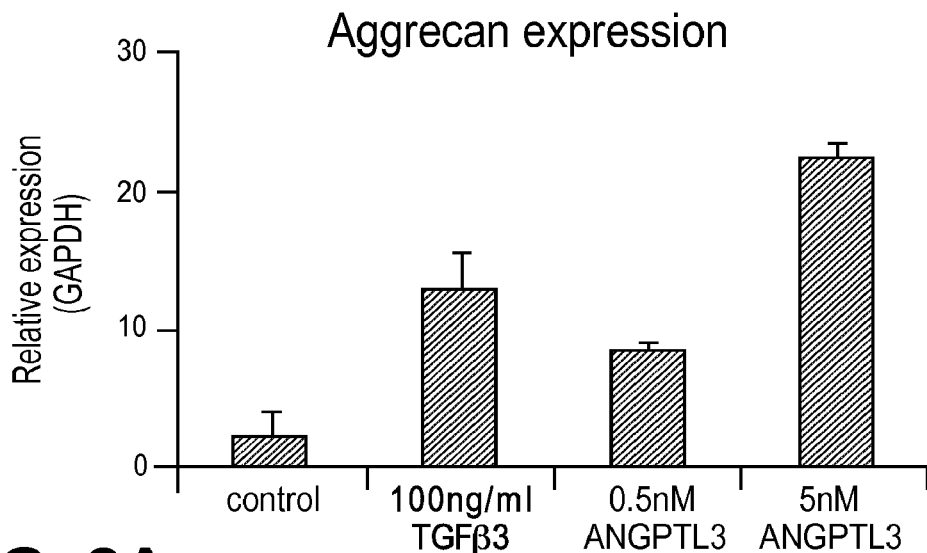
FIG. 2A. hMSCs were grown in pellet culture (1×106 cells/pellet) for 21 days in serum free DMEM, 1×ITS and ANGTPL3 (where indicated). The media was replaced every 3 days. Aggrecan mRNA expression was quantified using human Taqman specific probes according to the manufacturer's instructions (data pooled from 3 experiments in duplicate (n=6).
Figure 2B:
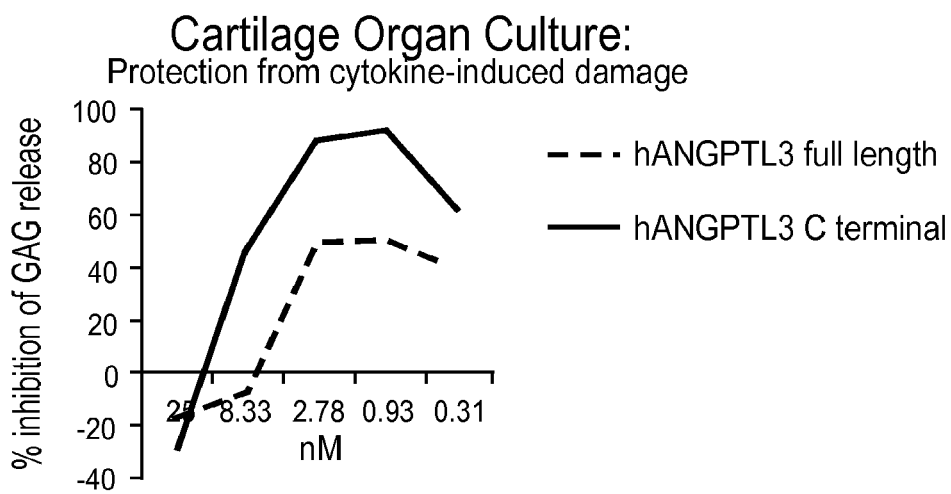
FIG. 2B. Bovine cartilage was isolated, punched into symmetric circles and put into organ culture. The slices were treated for 48 hours with 20 ng/ml TNFa and 10 ng/ml OSM (inflammatory mediators) to induce degradation of the cartilage matrix in the presence or absence of ANGPTL3 to identify the percent inhibition of glycosaminoglycan release, an indicator of matrix damage (data pooled from 4 donors, n=12).
Figure 2C:
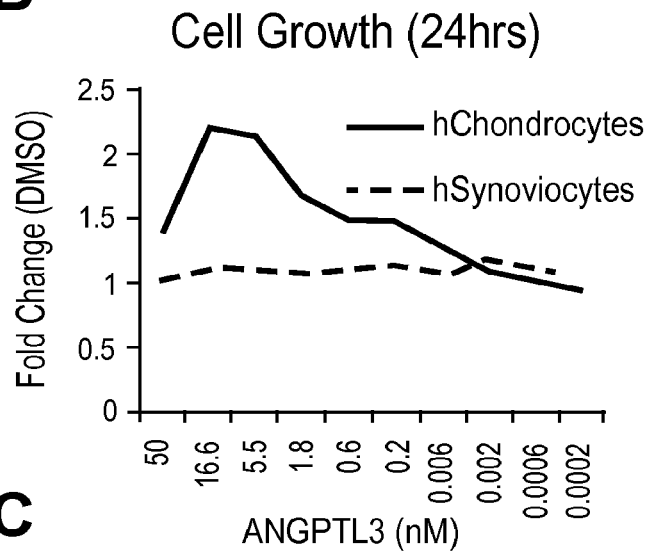
FIG. 2C. Primary normal human chondrocytes and synoviocytes (2500/384 well in growth media) were plated and cultured for 24 hrs at 37° C. A moderate chondrocyte-specific cell growth increase was demonstrated in response to ANGTPL3 over the 24 hr period (data pooled from 2 experiments, 2 replicates/dose (n=4)).

The mouse ANGPTL3 protein functions in mouse, human and bovine cell types and therefore was chosen for further characterization as it potently induced (0.5-5 nM) chondrogenic differentiation although its human homolog retains a similar potency for chondrogenesis compared to other previously know inducers of chondrogenesis in the quantitative imaged based type II collagen assay (FIG. 1). Both mouse and human MSCs differentiated in monolayer and pellet culture (respectively) for 18 to 21 days when treated with 0.5-5 nM ANGPTL3 and express three cartilage specific proteins: type II collagen, Sox9 and aggrecan. This was assessed by both immunohistochemical staining and mRNA quantification by Taqman (FIG. 2A). Additionally, data suggest after culturing mouse MSCs for 18 days, ANGPTL3 inhibits the spontaneous tendency towards a fibrotic repair response through reduced expression of alkaline phosphatase. To assess the potential ability to prevent tissue damage, bovine cartilage organ cultures were stimulated with TNFα and oncostatin M (OSM). The stimulated glycosaminoglycan release, an indicator of matrix degeneration, was significantly inhibited by treatment with ANGPTL3 (FIG. 2B). Additionally, treatment of primary human chondrocytes but not human synoviocytes led to a 2 fold increase in cell growth within 24 hrs (FIG. 2C) suggesting a specificity of its action on cartilage. The protein also had no obvious in vitro toxic effects (<100 μM) on the viability of in primary human chondrocytes, synovial fibroblasts and MSCs (data not shown).

In a direct comparison between the two candidates presently in clinical trials, treatment with 100 ng/ml of FGF18 or 100 ng/ml BMP7 could induce chondrogenic nodules, but with less overall matrix production compared to ANGPTL3. FGF18 lacked the ability to increase Alcian Blue, Sox9 or Type II collagen staining, indicating a lack of specificity of a true cartilage matrix. 100 ng/ml of BMP7 increased Alcian blue, Sox9 and Type II collagen staining, but the significance was not as great at similar concentrations.

Example 2: Expression of Recombinant Full Length ANGPTL3 and Mutant Protein and Function Analysis Mouse ANGPTL3 is predicted to be 51 kDa protein. It belongs to a family of 7 identified Angiopoietin-like (ANGPTL) proteins that have structural similarity to the angiopoiteins, but lack the ability to bind the Tie2 receptor and have distinct functions. They contain an N-terminal coiled-coil domain (CCD) and a C-terminal fibrinogen-like domain (FLD). ANGPTL proteins are tightly regulated by their microenvironment and interactions with the extracellular matrix (ECM), yet the precise interaction sites nor partners have been elucidated in detail. ANGPTL3 is secreted by the liver and circulates systemically. It is controlled through liver X receptors (LXR), with evidence that LXR-induced hyper-triglyceridmedia is due to ANGPTL3 release. Interactions between the CCD and the ECM through a putative heparin binding motif may lead to inhibition of cleavage at the proprotein convertase recognition sequence (R221-R224), similar to that reported for ANGPTL4. Cleavage results in a significant increase in the CCD's ability to inhibit lipoprotein lipase activity (LPL), and thereby leads to increase of triglyceridemia (TG). This represents the major biological function of ANGPTL3 identified prior to the present invention. The C terminal FLD is sufficient to induce endothelial cell adhesion and mediate angiogenesis after direct implantation in the rat cornea in vivo. It was also demonstrated that recombinant ANGPTL3 could bind to purified αVβ3 integrin and lead to an increase in FAK, MAPK and AKT signaling in endothelial cells. These data suggest the FLD interaction with integrins to mediate angiogenesis.

No expression of ANGPTL3 has been reported nor observed in our studies using western blotting in human chondrocytes, hMSCs or human synovial fibroblasts, and no expression of it was found in mouse knee joints. Furthermore, there are no reported activities for either fragment in joint cells relating to this novel chondrogenic function identified in our screen.

Figure 3A:
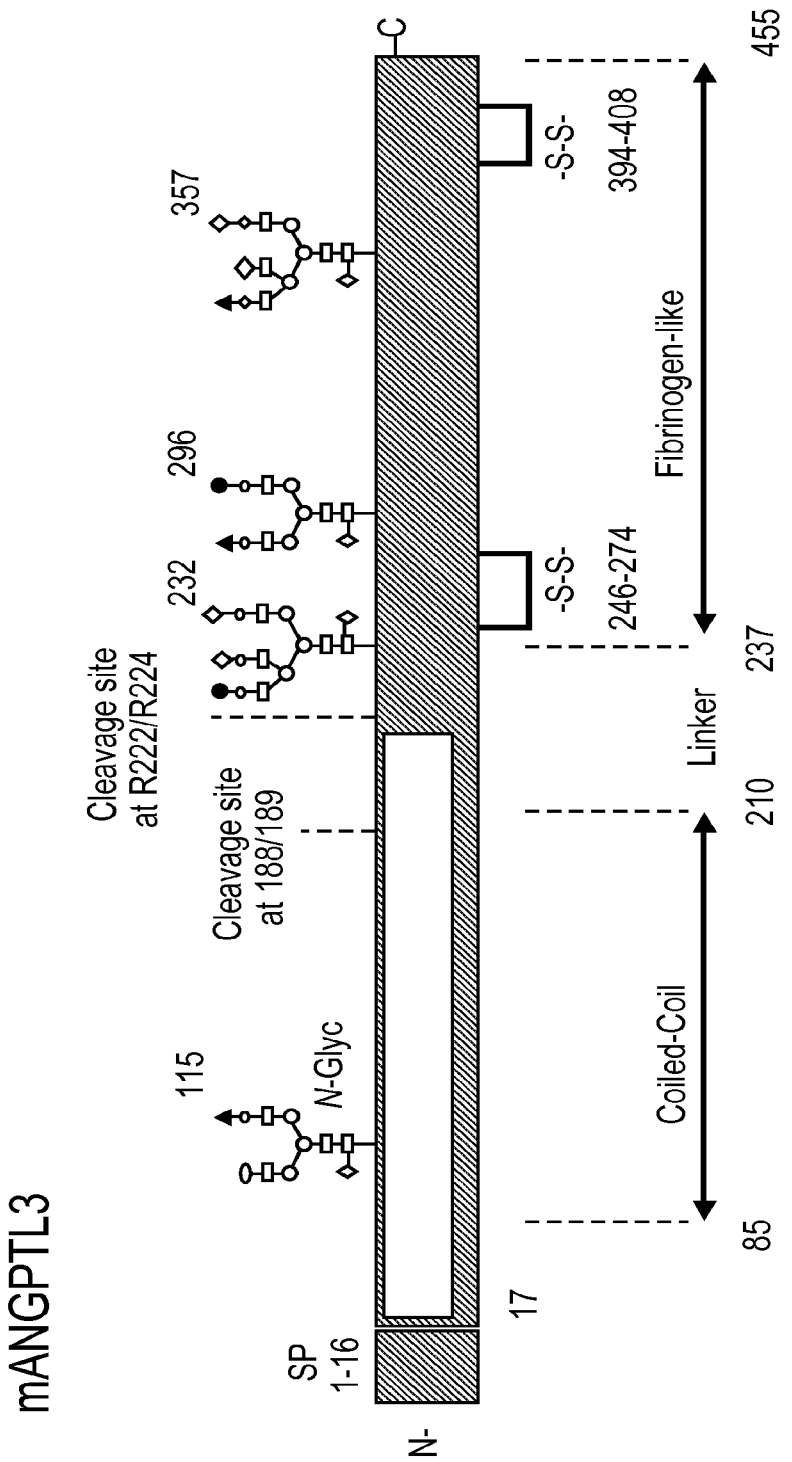
FIG. 3A. The primary protein structure and confirmed glycosylation sites.
Figure 3B:
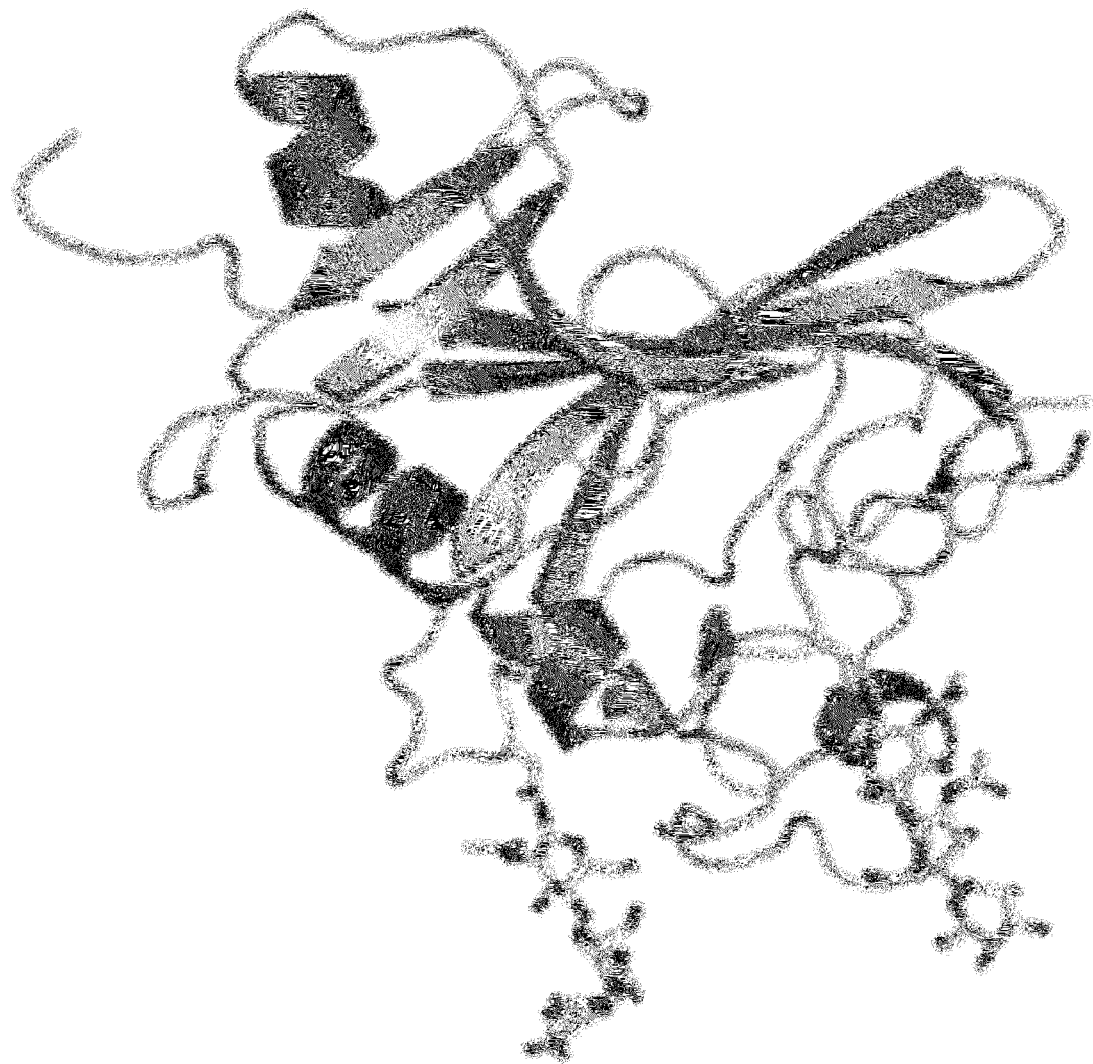
FIG. 3B. The atomic structure (1.8 angstroms) of mANGTPL3 the C-terminal FLD (225-455).

Our data indicates that full length ANGPTL3 is a novel mediator of chondrogenesis and cartilage protection. We examined which domains of ANGPTL3 are critical for this novel chondrogenic function. A truncation series of ANGPTL3 and full length protein have been expressed and purified in an engineered HEK-S cell line that gives limited and homogeneous glycosylation for detailed biophysical characterization. Mass spectrometric approaches confirmed the occupancy of all four predicted N-linked glycosylations (N115, N232, N296, and N357, FIG. 3A). From HEK endogenously processed fragments, the proteolytic cleavage site between the CCD and FLD domain was determined to be R224. The full length ANGPTL3 elutes by size exclusion chromatography with a mass >400 kDa, indicative of a trimer with heterogeneous glycosylation. The FLD (241-455), shown to be a monomer by size exclusion and static light scattering, was crystallized. The atomic structure of the FLD was determined at 1.8 angstroms resolution. The FLD structure revealed a core beta sheet configuration with helical stretches that orient three loops toward the C-terminus, typical of other FLD homologs (FIG. 3B). The temperature factors in the C-terminal portion of the domain are higher than the rest of the structure suggesting a high degree of flexibility in this region. Superposition with the ANGPTL2/Tie2 structure (PDB code: 2GY7) suggests that the C-terminal portion of the FLD may be involved in protein-protein interactions.

The five truncation products generated have been evaluated in multiple chondrogenic assays. The results suggests no activity retention in the CCD alone, but activity remains in the FLD. Additionally, SMAD1 phosphorylation is increased upon stimulation for 3 days with the full length or mutants G or H alone, suggesting activation of chondrogenic signaling cascade.

Although systemic exposure of a protein injected intra-articularly is limited due to the synovial fluid lymph drainage, minimizing systemic exposure can sometimes be desirable. If there is systemic exposure, the cleavage of ANGPTL3 might lead to the release the CCD domain. The increased inhibition of LPL activity by CCD could lead to alteration of the patients' TG levels. Our results indicate potential clinical advantages of ANGPTL3. For instance, by dissecting where the chondrogenic activity in ANGPTL3 is localized we would minimize or exclude the unwanted systemic effects on lipid metabolism or the angiogenic properties. The chondrogenic activity is localized primarily to the C terminus thus specific use of this domain would alleviate the concerns of TG regulation of the full length molecule or N terminus. As full length ANGPTL3 is normally present in serum, there is no expected immunogenicity. An additional advantage of using the C terminus is that it is cleaved and is a monomer (~29 kDa) compared to the trimerized full length protein, thus possibly reducing systemic half life of any small percentage which might be present in circulation and limiting any potential effect from angiogenesis.

Example 3: In Vivo Analysis of ANGPTL3

We have performed several in vivo evaluations of the full length ANGPTL3 to address potential adverse events and intra-articular retention. Following intra-articular (IA) injection of the left knee joints of 8 week old C57BL/10 mice with 3.6 µg of full length ANGPTL3, we evaluated immunohistochemically the expression in the presence and absence of exposure for 24 hours. By 24 hours, very little to no detectable levels of ANGPTL3 should remain in the synovial fluid as the typical turnover by trans-synovial flow into the synovial lymph vessels for proteins and water is approximately 2 hours. The results revealed no endogenous expression of ANGPTL3 in untreated joints, but significant detection of the protein in the pericellular matrix in the articular cartilage and in the menisci even at the 24 hour time point. Additionally no widespread cytotoxicity to the chondrocytes or cartilage damage in vivo was detected. Following a series of 3 IA injections into the knee joints of rats (once/week for three weeks), clinically there was no toxicity (no joint swelling or alternations in gait) or evidence of an acute inflammatory reaction in the joint of the rat. Histologically, there was no increase in synovitis or uncontrolled proliferation in the joints of the five rats injected. As in the mouse, ANGPTL3 could be detected in the cartilage matrix and surrounding the chondrocytes. These results indicate that ANGPTL3 does not cause any undesired effects to the cartilage itself. and that ANGPTL3 does enter into and is retained in cartilage and menisci in vivo.

Figure 5A:
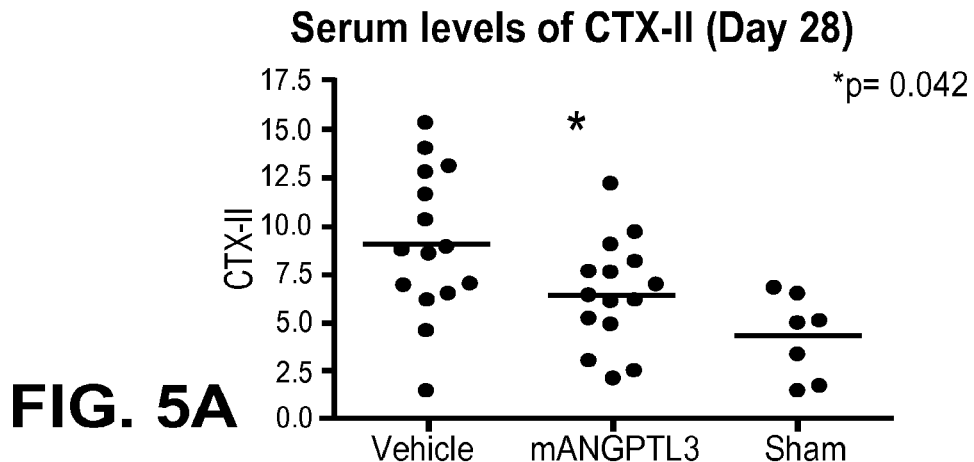
FIG. 5A. Peripheral blood was collected on day 28 following the surgery. The circulating type II collagen fragments (CTX-II) were quantified by an ELISA (Nordic biosciences). mANGPTL3 dose=200 ng/knee, 3 weekly injections.
Figure 5B:
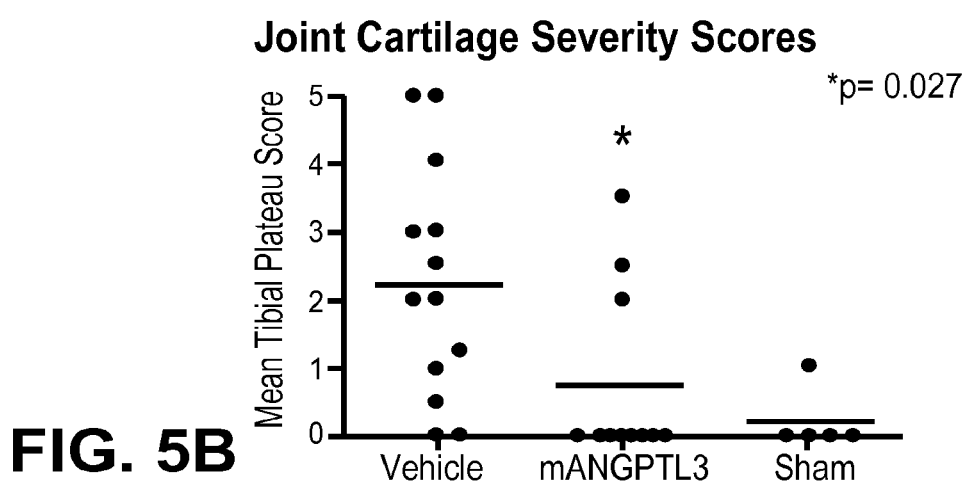
FIG. 5B. Quantitative assessments of the tibial plateau were made on a 0-4 scale, 0 being normal and 5 being severe OA (full thickness disruption of the cartilage). Two sections from each mouse were blindly graded by 2 observers. mANGPTL3 dose=200 ng/knee, 3 weekly injections.

OA is not a single disease entity and can be considered the consequence of various etiologic factors. In humans it is often caused by abnormal biomechanical stress or genetic or acquired abnormalities of the articular cartilage or bone. Therefore, choosing the "best" small animal OA model is difficult and multiple models should be explored to determine the protective properties of any therapeutic. We have completed efficacy studies a chronic OA model (collagenase VII-induced based upon the research described by van der Kraan and colleagues) and an acute surgical model involving transection of the three of the major ligaments (ACL, MCL and MMTL) in the joint based upon the work of Glasson et al. Both models induced pathological changes commonly associated with OA: loss of proteoglycan staining, erosion of the cartilage and bone, osteophyte formation and metaplastic alterations in the synovium and ligaments can be evident 4-8 weeks after initiation of OA. FIG. 5 depicts the regenerative capacity of ANGPTL3 surgical model of OA. To begin to examine potential biomarkers for OA, peripheral blood was collected during the surgical model to measure the type 11 collagen fragments released due to cartilage damage (FIG. 5A). Histological analysis and subsequent grading of the medial tibial plateau revealed regeneration in the cartilage matrix after treatment with 200 ng ANGTPL3/knee once per week for 3 weeks (FIG. 5B).

Figure 5C:
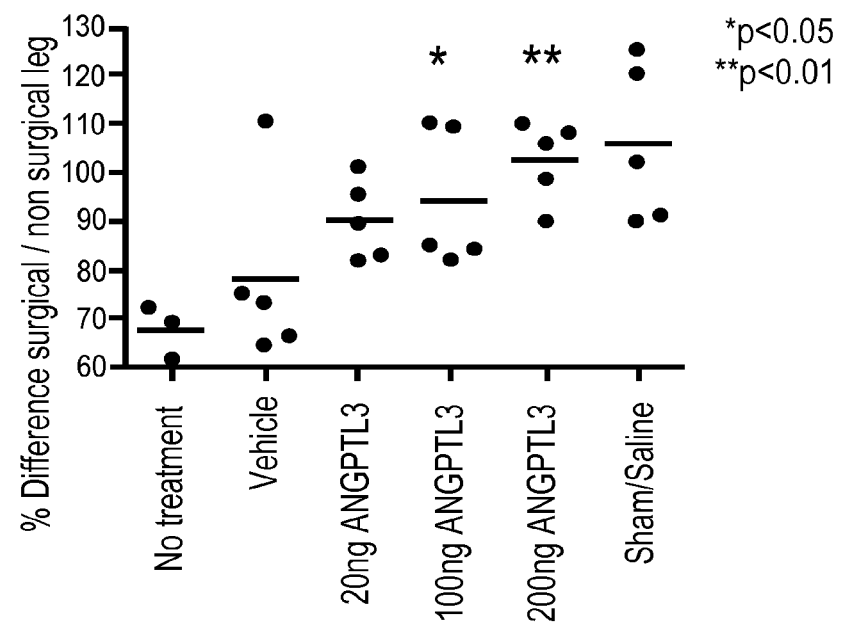
FIG. 5C. OA pain was measured by incapacitance testing, or determining the percentage of time the mouse stood on the surgical leg vs the other leg through the monitoring device. Readouts represent the pain response on day 36 after surgery (3 doses weekly doses of ANGPTL3 at the indicated concentration).

In a 8 week surgical OA subset of mice, three doses of ANGPTL3 were examined for alleviation of OA-induced pain through incapacitance measurements. This method measures the weight distribution between the surgical and non-surgical legs. On day 36 following surgery and 3 weekly treatments with PRO 1, as low as 100 ng/knee dosing demonstrated significant improvement compared to the vehicle treated surgical knees (FIG. 5C). These combined data provide concrete evidence that ANGTPL3 has in vivo efficacy in two OA models (both pathological correction and pain diminishment) and supports the advancement of its development as a novel OA therapeutic.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

SEQUENCE LISTING

SEQ ID NO: 1
241-455 consensus
XXPAXCXXXXYNXGXHTSGXYXIXPXNSQXFXVYCDXXSGSXWTLIQHRXDGSQXFNETWENY
XXGFGRLDGEFWLGLEKIYXIVXQSNYXLRXELXDWXD(X) KXYXEYXFXLGXHETNYTLHX

SEQUENCE LISTING

```
XXIXGNXXXAXPEXXDLXFSTWXHXAKGXXXXCPEXXSGGWWXXXXCGENNLNGKYNKXXXKX
XPERXXGXXWXXQXXXLYXIKXXKMXXXPXX

SEQ ID NO: 2
225-455 consensus
TTPXXXXNEXXNXXXXXXPAXCXXXXYNXGXHTSGXYXIXPXNSQXFXVYCDXXSGSXWTLIQ
HRXDGSQXFNETWENYXXGFGRLDGEFWLGLEKIYXIVXQSNYXLRXELXDWXD(X)KXYXE
YXFXLGXHETNYTLHXXXIXGNXXXAXPEXXDLFSTWXHXAKGXXXXCPEXXSGGWWXXXXC
GENNLNGKYNKXXXKXXPERXXGXXWXXQXXXLYXIKXXKMXXXPXX SEQ ID NO: 3
207-455 consensus
XIXEXXEXSLSSKXRAPRTTPXXXXNEXXNXXXXXXPAXCXXXXYNXGXHTSGXYXIXPXNSQ
XFXVYCDXXSGSXWTLIQHRXDGSQXFNETWENYXXGFGRLDGEFWLGLEKIYXIVXQSNYX
LRXELXDWXD(X)KXYXEYXFXLGXHETNYTLHXXXIXGNXXXAXPEXXDLFSTWXHXAKG
XXXXCPEXXSGGWWXXXXCGENNLNGKYNKXXXKXXPERXXGXXWXXQXXXLYXIKXXKMXXX
PXX SEQ ID NO: 4
Full length consensus
MXTIKLXLXXXPLVIXSXXDXDXXSXDSXXXEPKSRFAMLDDVKILANGLLQLGHGLKDFVH
KTKGQINDIFQKLNIFDQSFYDLSLXTXEIKEEEKELRRXTXXLQVKNEEVKNMSXELXSKX
ESLLEEKXXLQXKVXXLEXQLPXLIXXXXXXXXEXXEVTSLKXXVEXQDNSIXXLLQXVEXQY
XQLXQQXXQIKEIEXQLR(X)XXIXEXXEXSLSSKXRAPRTTPXXXXNEXXNXXXXXXPAXC
XXXXYNXGXHTSGXYXIXPXNSQXFXVYCDXXSGSXWTLIQHRXDGSQXFNETWENYXXGFGR
LDGEFWLGLEKIYXIVXQSNYXLRXELXDWXD(X)KXYXEYXFXLGXHETNYTLHXXXIXGN
XXXAXPEXXDLFSTWXHXAKGXXXXCPEXXSGGWWXXXXCGENNLNGKYNKXXXKXXPERXX
GXXWXXQXXXLYXIKXXKMXXXPXX(SEXXE)

SEQ ID NO: 5
Human ANGPTL3 241-455
GIPAECTTIYNRGEHTSGMYAIRPSNSQVFHVYCDVISGSPWTLIQHRIDGSQNFNETWENY
KYGEGRLDGEFWLGLEKIYSIVKQSNYVLRIELEDWKDNKHYIEYSFYLGNHETNYTLHLVA
ITGNVPNAIPENKDLVFSTWDHKAKGHFNCPEGYSGGWWWHDECGENNLNGKYNKPRAKSKP
ERRRGLSWKSQNGRLYSIKSTKMLIHPTD SEQ ID NO 6
Human ANGPTL3 225-455
TTPFLQLNEIRNVKHDGIPAECTTIYNRGEHTSGMYAIRPSNSQVFHVYCDVISGSPWTLIQ
HRIDGSQNFNETWENYKYGFGRLDGEFWLGLEKIYSIVKQSNYVLRIELEDWKDNKHYIEYS
FYLGNHETNYTLHLVAITGNVPNAIPENKDLVFSTWDHKAKGHENCPEGYSGGWWWHDECGE
NNLNGKYNKPRAKSKPERRRGLSWKSQNGRLYSIKSTKMLIHPTD SEQ ID NO 7
Human ANGPTL3 207-455
IQEPTEISLSSKPRAPRTTPFLQLNEIRNVKHDGIPAECTTIYNRGEHTSGMYAIRPSNSQV
FHVYCDVISGSPWTLIQHRIDGSQNFNETWENYKYGFGRLDGEFWLGLEKIYSIVKQSNYVL
RIELEDWKDNKHYIEYSFYLGNHETNYTLHLVAITGNVPNAIPENKDLVFSTWDHKAKGHFN
CPEGYSGGWWWHDECGENNLNGKYNKPRAKSKPERRRGLSWKSQNGRLYSIKSTKMLIHPTD SEQ ID NO 8
Full length human ANGPTL3 gi|7656888|ref|NP_055310.1| [Homo
sapiens]
MFTIKLLLFIVPLVISSRIDQDNSSEDSLSPEPKSRFAMLDDVKILANGLLQLGHGLKDEVH
KTKGQINDIFQKLNIFDQSFYDLSLQTSEIKEEEKELRRTTYKLQVKNEEVKNMSLELNSKL
ESLLEEKILLQQKVKYLEEQLTNLIQNQPETPERPEVTSLKTFVEKQDNSIKDLLQTVEDQY
KQLNQQHSQIKEIENQLRRTSIQEPTEISLSSKPRAPRTTPFLQLNEIRNVKHDGIPAECTT
IYNRGEHTSGMYAIRPSNSQVFHVYCDVISGSPWTLIQHRIDGSQNFNETWENYKYGEGRLD
GEFWLGLEKIYSIVKQSNYVLRIELEDWKDNKHYIEYSFYLGNHETNYTLHLVAITGNVPNA
IPENKDLVFSTWDHKAKGHFNCPEGYSGGWWWHDECGENNLNGKYNKPRAKSKPERRRGLSW
KSQNGRLYSIKSTKMLIHPTDSESFE SEQ ID NO: 9
Mouse ANGPTL3 241-455
DLPADCSAVYNRGEHTSGVYTIKPRNSQGFNVYCDTQSGSPWTLIQHRKDGSQDFNETWENY
EKGEGRLDGEFWLGLEKIYAIVQQSNYILRLELQDWKDSKHYVEYSFHLGSHETNYTLHVAE
IAGNIPGALPEHTDLMFSTWNHRAKGQLYCPESYSGGWWWNDICGENNLNGKYNKPRTKSRP
ERRRGIYWRPQSRKLYAIKSSKMMLQPTT SEQ ID NO 10
Mouse ANGPTL3 225-455
TTPPLQLNETENTEQDDLPADCSAVYNRGEHTSGVYTIKPRNSQGENVYCDTQSGSPWTLIQ
HRKDGSQDFNETWENYEKGFGRLDGEFWLGLEKIYAIVQQSNYILRLELQDWKDSKHYVEYS
FHLGSHETNYTLHVAEIAGNIPGALPEHTDLMESTWNHRAKGQLYCPESYSGGWWWNDICGE
NNLNGKYNKPRTKSRPERRRGIYWRPQSRKLYAIKSSKMMLQPTT
```

SEQUENCE LISTING

```
SEQ ID NO 11
Mouse ANGPTL3 207-455
IQEPSENSLSSKSRAPRTTPPLQLNETENTEQDDLPADCSAVYNRGEHTSGVYTIKPRNSQG
FNVYCDTQSGSPWTLIQHRKDGSQDFNETWENYEKGFGRLDGEFWLGLEKIYAIVQQSNYIL
RLELQDWKDSKHYVEYSFHLGSHETNYTLHVAEIAGNIPGALPEHTDLMFSTWNHRAKGQLY
CPESYSGGWWWNDICGENNLNGKYNKPRTKSRPERRRGIYWRPQSRKLYAIKSSKMMLQPTT SEQ ID NO 12
Full length mouse ANGPTL3 gi|33469117|ref|NP_038941.1| [Mus
musculus]
MHTIKLFLEVVPLVIASRVDPDLSSFDSAPSEPKSRFAMLDDVKILANGLLQLGHGLKDFVH
KTKGQINDIFQKLNIFDQSFYDLSRTNEIKEEEKELRRTTSTLQVKNEEVKNMSVELNSKL
ESLLEEKTALQHKVRALEEQLTNLILSPAGAQEHPEVTSLKSFVEQQDNSIRELLQSVEEQY
KQLSQQHMQIKEIEKQLRKTGIQEPSENSLSSKSRAPRTTPPLQLNETENTEQDDLPADCSA
VYNRGEHTSGVYTIKPRNSQGFNVYCDTQSGSPWTLIQHRKDGSQDFNETWENYEKGFGRLD
GEFWLGLEKIYAIVQQSNYILRLELQDWKDSKHYVEYSFHLGSHETNYTLHVAEIAGNIPGA
LPEHTDLMFSTWNHRAYGQLYCPESYSGGWWWNDICGENNLNGKYNKPRTKSRPERRRGIYW
RPQSRKLYAIKSSKMMLQPTT SEQ ID NO: 13
Bovine ANGPTL3 241-454
DIPADCTIIYNQGKHTSGIYSIRPSNSQVFNVYCDVKSGSSWTLIQHRIDGSQNFNETWENY
KYGFGRLDGEFWLGLEKIYSIVMQSNYILRIELEDWKDYYTEYSFHLGDHETNYTLHLAEI
SGNGPKAFPEHKDLMFSTWDHKAKGHFNCPESNSGGWWYHDVCGENNLNGKYNKPKAKAKPE
RKEGICWKSQDGRLYSIKATKMLIHPSD SEQ ID NO 14
Bovine ANGPTL3 225-454
TTPSFHSNETKNVEHDDIPADCTIIYNQGKHTSGIYSIRPSNSQVFNVYCDVKSGSSWTLIQ
HRIDGSQNFNETWENYKYGFGRLDGEFWLGLEKIYSIVMQSNYILRIELEDWKDKYYTEYSF
HLGDHETNYTLHLAEISGNGPKAFPEHKDLMFSTWDHKAKGHFNCPESNSGGWWYHDVCGEN
NLNGKYNKPKAKAKPERKEGICWKSQDGRLYSIKATKMLIHPSD SEQ ID NO 15
Bovine ANGPTL3 207-454
IKESTEISLSSKPRAPRTTPSFHSNETKNVEHDDIPADCTIIYNQGKHTSGIYSIRPSNSQV
FNVYCDVKSGSSWTLIQHRIDGSQNFNETWENYKYGFGRLDGEFWLGLEKIYSIVMQSNYIL
RIELEDWKDKYYTEYSFHLGDHETNYTLHLAEISGNGPKAFPEHKDLMFSTWDHKAKGHFNC
PESNSGGWWYHDVCGENNLNGKYNKPKAKAKPERKEGICWKSQDGRLYSIKATKMLIHPSD SEQ ID NO 16
Full length bovine ANGPTL3 gi|122692391|ref|NP_001073814.1|
[Bos taurus]
MYTIKLFLIIAPLVISSRTDQDYTSLDSISPEPKSRFAMLDDVKILANGLLQLGHGLKDFVH
KTKGQINDIFQKLNIFDQSFYDLSLQTNEIKEEEKELRRATSKLQVKNEEVKNMSLELDSKL
ESLLEEKILLQQKVRYLEDQLTDLIKNQPQIQEYLEVTSLKTLVEQQDNSIKDLLQIVEEQY
RQLNQQQSQIKEIENQLRRTGIKESTEISLSSKPRAPRTTPSFHSNETKNVEHDDIPADCTI
IYNQGKHTSGIYSIRPSNSQVFNVYCDVKSGSSWTLIQHRIDGSQNFNETWENYKYGFGRLD
GEFWLGLEKIYSIVMQSNYILRIELEDWKDKYYTEYSFHLGDHETNYTLHLAEISGNGPKAF
PEHKDLMFSTWDHKAKGHFNCPESNSGGWWYHDVCGENNLNGKYNKPKAKAKPERKEGICWK
SQDGRLYSIKATKNILIHPSDSENSE SEQ ID NO: 17
Canine ANGPTL3 240-454
DIPANCTTIYNRGEHTSGIYSIRPSNSQVFNVYCDVKSGSSWTLIQHRIDGSQNFNETWENY
RYGFGRLDGEFWLGLEKIYSIVKQSNYILRIELEDWNDNKHYIEYFFHLGNHETNYTLHLVE
ITGNILNALPEHKDLVFSTWDHKAKGHVNCPESYGGWWWHNVCGENNLNGKYNKQRAKTKP
ERRRGLYWKSQNGRLYSIKSTKMLIHPID SEQ ID NO: 18
Canine ANGPTL3 224-454
TTPFLHLNETKNVEHNDIPANCTTIYNRGEHTSGIYSIRPSNSQVFNVYCDVKSGSSWTLIQ
HRIDGSQNFNETWENYRYGFGRLDGEFWLGLEKIYSIVKQSNYILRIELEDWNDNKHYIEYF
FHLGNHETNYTLHLVEITGNILNALPEHKDLVFSTWDHKAKGHVNCPESYGGWWWHNVCGE
NNLNGKYNKQRAKTKPERRRGLYWKSQNGRLYSIKSTKMLIHPID SEQ ID NO: 19
Canine ANGPTL3 206-454
IQESTENSLSSKPRAPRTTPFLHLNETKNVEHNDIPANCTTIYNRGEHTSGIYSIRPSNSQV
FNVYCDVKSGSSWTLIQHRIDGSQNFNETWENYRYGFGRLDGEFWLGLEKEYSIVKQSNYIL
RIELEDWNDNKHYIEYFFHLGNHETNYTLHLVEITGNILNALPEHKDLVFSTWDHKAKGHVN
CPESYGGWWWHNVCGENNLNGKYNKQRAKTKPERRRGLYWKSQNGRLYSIKSTKMLIHPID
```

SEQUENCE LISTING

SEQ ID NO: 20
Full length canine ANGPTL3 gi|57086505|ref|XP_536686.1| [Canis familiaris]
MYTIKLFLFIIPLVISSKIDRDYSSYDSVSPEPKSRFAMLDDVKILANGLLQLGHGLKDFVH
KTKGQINDIFQKLNIFDQSFYDLSLQTNEIKEEEKELRRTTSKLQVKNEEVKNMSLELNSKV
ESLLEEKILLQQKVRYLEKQLTSLIKNQPEIQEHPEVTSLKTFVEQQDNSIKDLLQTVEEQY
RQLNQQHSQIKEIENQLRNVIQESTENSLSSKPRAPRTTPFLHLNETKNVEHNDIPANCTTI
YNRGEHTSGIYSIRPSNSQVFNVYCDVKSGSSWTLIQHRIDGSQNFNETWENYRYGFGRLDG
EFWLGLEKIYSIVKQSNYILRIELEDWNDNKHYIEYFFHLGNHETNYTLHLVEITGNILNAL
PEHKDLVFSTWDHKAKGHVNCPESYSGGWWWHNVCGENNLNGKYNKQRAKTKPERRRGLYWK
SQNGRLYSIKSTKMLIHPIDSESSE SEQ ID NO: 21
Equine ANGPTL3 241-455
DFPADCTTIYNRGEHTSGIYSIKPSNSQVFNVYCDVISGSSWILIQRRIDGSQNFNETWQNY
KYGEGRLDFEFWLGLEKIYSIVKRSNYILRIELEDWKDNKHTIEYSFHLGNHETNYTLHLVE
ITGNVPNALPEHKDLVESTWDHKAKGQLNCLESYSGGWWWHDVCGGDNPNGKYNKFRSKTKP
ERRRGICWKSQNGRLYTIKSTKML1HPID SEQ ID NO: 22
Equine ANGPTL3 225-455
TTPSFHLNETKDVEHDDFPADCTTIYNRGEHTSGIYSIKPSNSQVFNVYCDVISGSSWILIQ
RRIDGSQNFNETWQNYKYGFGRLDFEFWLGLEKIYSIVKRSNYILRIELEDWKDNKHTIEYS
FHLGNHETNYTLHLVEITGNVPNALPEHKDLVFSTWDHKAKGQLNCLESYSGGWWWHDVCGG
DNPNGKYNKPRSKTKPERRRGICWKSQNGRLYTIKSTKMLIHPID SEO ID NO: 23
Equine ANGPTL3 207-455
IQESTENSLSSKPRAPRTTPSFHLNETKDVEHDDFPADCTTIYNRGEHTSGIYSIKPSNSQV
FNVYCDVISGSSWILIQRRIDGSQNFNETWQNYKYGPGRLDFEFWLGLEKIYSIVKRSNYIL
RIELEDWKDNKHTIEYSFHLGNHETNYTLHLVEITGNVPNALPEHKDLVFSTWDHKAKGQLN
CLESYSGGWWWHDVCGGDNPNGKYNKPRSKTKPERRRGICWKSQNGRLYTIKSTKMLIHPID SEQ ID NO: 24
Full length equine ANGPTL3 [equus caballus]
MYTIKLFLVIAPLVISSRIDQDYSSLDSIPPEPKSRFAMLDDVKILANGLLQLGHGLKDFVH
KTKGQINDIFQKLNIFDQSFYALSLQTNEIKEEEKELRRTTSKLQVKNEEVKNMSLELNSKL
ESLLEEKSLLQQKVKYLEEQLTKLIKNQPEIQEHPEVTSLKTFVEQQDNSIKDLLQTMEEQY
RQLNQQHSQIKEIENQLRRTGIQESTENSLSSKPRAPRTTPSFHLNETKDVEHDDFPADCTT
IYNRGEHTSGIYSIKPSNSQVFNVYCDVISGSSWILIQRRIDGSQNFNETWQNYKYGFGRLD
FEFWLGLEKIYSIVKRSNYILRIELEDWKDNKHTIEYSFHLGNHETNYTLHLVEITGNVPNA
LPEHKDLVFSTWDHKAKGQLNCLESYSGGWWWHDVCGGDNPNGKYNKPRSKTKPERRRGICW
KSQNGRLYTIKSTKMLIHPIDSESFELRQIKKPMN SEQ ID NO: 25
241-455 consensus
XXPAXCXXXYNXGXHTSGXYXIXPXNSQXFXVYCDXXSGSXWLIQXRXDGSQXFNETWXNY
XXGFGRLDXEFWLGLEKIYKIVXXSNYXLEXELXDWXD(X)KXXXEYXFXLGXHETNYTLHX
XXIXGNXXXAXPEXXDLXFSTWXHXAKGXXXCXEXXSGGWWXXXXCGXXNXNGKYNKXXXKX
XPERXXGXXWXXQXXXLYXIKXXKMXXXPXX SEQ ID NO: 26
225-455 consensus
TTPXXXXNEXXXXXXXXXPAXCXXXYNXGXHTSGXYXIXPXNSQXFXVYCDXXSGSXWLIQ
XRXDGSQXFNETWXNYXXGFGRLDXEFWLGLEKIYXIVXXSNYXLEXELXDWXD(X)KXXXE
YXFXLGXHETNYTLHXXXIXGNXXXAXPEXXDLXFSTWXHXAKGXXXCXEXXSGGWWXXXXC
GXXNXNGKYNKXXXKXXPERXXGXXWXXQXXXLYXIKXXKMXXXPXX SEQ ID NO: 27
207-455 consensus
XIXEXXEXSLSSKXRAPRTTPXXXXNEXXXXXXXXXPAXCXXXYNXGXHTSGXYXIXPXNSQ
XFXVYCDXXSGSXWLIQXRXDGSQXFNETWXNYXXGFGRLDXEFWLGLEKIYXIVXXSNYX
LEXELXDWXD(X)KXXXEYXFXLGXHETNYTLHXXXIXGNXXXAXPEXXDLXFSTWXHXAKG
XXXCXEXXSGGWWXXXXCGXXNXNGKYNKXXXKXXPERXX0XXWXXQXXXLYXIKXXKMXXX
PXX

SEQUENCE LISTING

SEQ ID NO: 28
Full length consensus
MXTIKLXLXXXPLVIXSXXDXDXXSXDSXXXEPKSRFAMLDDVKILANGLLQLGHGLKDEVH
KTKGQINDIFQKLNIFDQSFYXLSLXTXEIKEEEKELRRXTXXLQVKNEEVKNMSXELXSKX
ESLLEEKXXLQXKVXXLEXQLTXLIXXXXXXXXEXXEVTSLKXXVEXQDNSIXXLLQXXEXQY
XQLXQQXXQIKEIEXQLR(X)XXIXEXXEXSLSSKXRAPRTTPXXXXNEXXXXXXXXXPAXC
XXXYNXGXHTSGXYXIXPXNSQXFXVYCDXXSGSXWXLIQXRXDGSQXFNETWXNYXXGFGR
LDXEFWLGLEKIYXIVXXSNYXLEXELXDWXD(X)KXXXEYXFXLGXHETNYTLHXXXIXGN
XXXAXPEXXDLXFSTWXHXAKGXXXCXEXXSGGWWXXXXCGXXNXNGKYNKXXXKXXPERXX
GXXWXXQXXXLYXIKXXKMXXXPXX(SEXXEXXXXXXXX)

X = any am

```
<210> SEQ ID NO 2
<211> LENGTH: 231
<212> TYPE: PRT
<213> ORGANISM: Artificial Sequence
<220> FEATURE:
<223> OTHER INFORMATION: Consensus sequence for amino acids 225-455 of
      human, mouse, bovine and canine ANGPTL3 polypeptide
<220> FEATURE:
<221> NAME/KEY: misc_feature
<222> LOCATION: (1)..(231)
<223> OTHER INFORMATION: "X" = any amino acid

<400> SEQUENCE: 2

Thr Thr Pro Xaa Xaa Xaa Asn Glu Xaa Xaa Asn Xaa Xaa Xaa Xaa
1               5                   10                  15

Xaa Xaa Pro Ala Xaa Cys Xaa Xaa Xaa Tyr Asn Xaa Gly Xaa His Thr
            20                  25                  30

Ser Gly Xaa Tyr Xaa Ile Xaa Pro Xaa Asn Ser Gln Xaa Phe Xaa Val
        35                  40                  45

Tyr Cys Asp Xaa Xaa Ser Gly Ser Xaa Trp Thr Leu Ile Gln His Arg
50              55                  60

Xaa Asp Gly Ser Gln Xaa Phe Asn Glu Thr Trp Glu Asn Tyr Xaa Xaa
65                  70                  75                  80

Gly Phe Gly Arg Leu Asp Gly Glu Phe Trp Leu Gly Leu Glu Lys Ile
                85                  90                  95

Tyr Xaa Ile Val Xaa Gln Ser Asn Tyr Xaa Leu Arg Xaa Glu Leu Xaa
            100                 105                 110

Asp Trp Xaa Asp Xaa Lys Xaa Tyr Xaa Glu Tyr Xaa Phe Xaa Leu Gly
            115                 120                 125

Xaa His Glu Thr Asn Tyr Thr Leu His Xaa Xaa Xaa Ile Xaa Gly Asn
    130                 135                 140

Xaa Xaa Xaa Ala Xaa Pro Glu Xaa Xaa Asp Leu Xaa Phe Ser Thr Trp
145                 150                 155                 160

Xaa His Xaa Ala Lys Gly Xaa Xaa Xaa Cys Pro Glu Xaa Xaa Ser Gly
            165                 170                 175

Gly Trp Trp Xaa Xaa Xaa Xaa Cys Gly Glu Asn Asn Leu Asn Gly Lys
            180                 185                 190

Tyr Asn Lys Xaa Xaa Xaa Lys Xaa Xaa Pro Glu Arg Xaa Xaa Gly Xaa
            195                 200                 205

Xaa Trp Xaa Xaa Gln Xaa Xaa Xaa Leu Tyr Xaa Ile Lys Xaa Xaa Lys
    210                 215                 220

Met Xaa Xaa Xaa Pro Xaa Xaa
225                 230

<210> SEQ ID NO 3
<211> LENGTH: 249
<212> TYPE: PRT
<213> ORGANISM: Artificial Sequence
<220> FEATURE:
<223> OTHER INFORMATION: Consensus sequence for amino acids 207-455 of
      human, bovine, mouse and canine ANGPTL3 polypeptide
<220> FEATURE:
<221> NAME/KEY: misc_feature
<222> LOCATION: (1)..(249)
<223> OTHER INFORMATION: "X" = any amino acid

<400> SEQUENCE: 3

Xaa Ile Xaa Glu Xaa Xaa Glu Xaa Ser Leu Ser Ser Lys Xaa Arg Ala
1               5                   10                  15
```

```
Pro Arg Thr Thr Pro Xaa Xaa Xaa Xaa Asn Glu Xaa Asn Xaa Xaa
                20                  25              30

Xaa Xaa Xaa Xaa Pro Ala Xaa Cys Xaa Xaa Xaa Tyr Asn Xaa Gly Xaa
            35              40              45

His Thr Ser Gly Xaa Tyr Xaa Ile Xaa Pro Xaa Asn Ser Gln Xaa Phe
 50                  55              60

Xaa Val Tyr Cys Asp Xaa Xaa Ser Gly Ser Xaa Trp Thr Leu Ile Gln
65              70              75                  80

His Arg Xaa Asp Gly Ser Gln Xaa Phe Asn Glu Thr Trp Glu Asn Tyr
             85                  90              95

Xaa Xaa Gly Phe Gly Arg Leu Asp Gly Glu Phe Trp Leu Gly Leu Glu
            100             105             110

Lys Ile Tyr Xaa Ile Val Xaa Gln Ser Asn Tyr Xaa Leu Arg Xaa Glu
            115             120             125

Leu Xaa Asp Trp Xaa Asp Xaa Lys Xaa Tyr Xaa Glu Tyr Xaa Phe Xaa
        130             135             140

Leu Gly Xaa His Glu Thr Asn Tyr Thr Leu His Xaa Xaa Xaa Ile Xaa
145             150             155                 160

Gly Asn Xaa Xaa Xaa Ala Xaa Pro Glu Xaa Xaa Asp Leu Xaa Phe Ser
            165             170             175

Thr Trp Xaa His Xaa Ala Lys Gly Xaa Xaa Xaa Cys Pro Glu Xaa Xaa
            180             185             190

Ser Gly Gly Trp Trp Xaa Xaa Xaa Cys Gly Glu Asn Asn Leu Asn
            195             200             205

Gly Lys Tyr Asn Lys Xaa Xaa Xaa Lys Xaa Xaa Pro Glu Arg Xaa Xaa
210             215             220

Gly Xaa Xaa Trp Xaa Xaa Gln Xaa Xaa Xaa Leu Tyr Xaa Ile Lys Xaa
225             230             235             240

Xaa Lys Met Xaa Xaa Xaa Pro Xaa Xaa
            245

<210> SEQ ID NO 4
<211> LENGTH: 460
<212> TYPE: PRT
<213> ORGANISM: Artificial Sequence
<220> FEATURE:
<223> OTHER INFORMATION: Consensus sequence for full-length human,
      bovine, mouse and canine ANGPTL3 polypeptide
<220> FEATURE:
<221> NAME/KEY: misc_feature
<222> LOCATION: (1)..(460)
<223> OTHER INFORMATION: "X" = any amino acid

<400> SEQUENCE: 4

Met Xaa Thr Ile Lys Leu Xaa Leu Xaa Xaa Xaa Pro Leu Val Ile Xaa
1               5                   10                  15

Ser Xaa Xaa Asp Xaa Asp Xaa Xaa Ser Xaa Asp Ser Xaa Xaa Xaa Glu
            20              25              30

Pro Lys Ser Arg Phe Ala Met Leu Asp Asp Val Lys Ile Leu Ala Asn
            35              40              45

Gly Leu Leu Gln Leu Gly His Gly Leu Lys Asp Phe Val His Lys Thr
 50              55              60

Lys Gly Gln Ile Asn Asp Ile Phe Gln Lys Leu Asn Ile Phe Asp Gln
65              70              75                  80

Ser Phe Tyr Asp Leu Ser Leu Xaa Thr Xaa Glu Ile Lys Glu Glu
             85              90              95

Lys Glu Leu Arg Arg Xaa Thr Xaa Xaa Leu Gln Val Lys Asn Glu Glu
```

```
                100             105             110
Val Lys Asn Met Ser Xaa Glu Leu Xaa Ser Lys Xaa Glu Ser Leu Leu
            115             120             125
Glu Glu Lys Xaa Xaa Leu Gln Xaa Lys Val Xaa Xaa Leu Glu Xaa Gln
            130             135             140
Leu Thr Xaa Leu Ile Xaa Xaa Xaa Xaa Xaa Xaa Glu Xaa Xaa Glu
145             150             155             160
Val Thr Ser Leu Lys Xaa Xaa Val Glu Xaa Gln Asp Asn Ser Ile Xaa
                165             170             175
Xaa Leu Leu Gln Xaa Val Glu Xaa Gln Tyr Xaa Gln Leu Xaa Gln Gln
            180             185             190
Xaa Xaa Gln Ile Lys Glu Ile Glu Xaa Gln Leu Arg Xaa Xaa Xaa Ile
            195             200             205
Xaa Glu Xaa Xaa Glu Xaa Ser Leu Ser Ser Lys Xaa Arg Ala Pro Arg
            210             215             220
Thr Thr Pro Xaa Xaa Xaa Xaa Asn Glu Xaa Xaa Asn Xaa Xaa Xaa Xaa
225             230             235             240
Xaa Xaa Pro Ala Xaa Cys Xaa Xaa Tyr Asn Xaa Gly Xaa His Thr
            245             250             255
Ser Gly Xaa Tyr Xaa Ile Xaa Pro Xaa Asn Ser Gln Xaa Phe Xaa Val
            260             265             270
Tyr Cys Asp Xaa Xaa Ser Gly Ser Xaa Trp Thr Leu Ile Gln His Arg
            275             280             285
Xaa Asp Gly Ser Gln Xaa Phe Asn Glu Thr Trp Glu Asn Tyr Xaa Xaa
            290             295             300
Gly Phe Gly Arg Leu Asp Gly Glu Phe Trp Leu Gly Leu Glu Lys Ile
305             310             315             320
Tyr Xaa Ile Val Xaa Gln Ser Asn Tyr Xaa Leu Arg Xaa Glu Leu Xaa
                325             330             335
Asp Trp Xaa Asp Xaa Lys Xaa Tyr Xaa Glu Tyr Xaa Phe Xaa Leu Gly
            340             345             350
Xaa His Glu Thr Asn Tyr Thr Leu His Xaa Xaa Xaa Ile Xaa Gly Asn
            355             360             365
Xaa Xaa Xaa Ala Xaa Pro Glu Xaa Xaa Asp Leu Xaa Phe Ser Thr Trp
            370             375             380
Xaa His Xaa Ala Lys Gly Xaa Xaa Xaa Cys Pro Glu Xaa Xaa Ser Gly
385             390             395             400
Gly Trp Trp Xaa Xaa Xaa Xaa Cys Gly Glu Asn Asn Leu Asn Gly Lys
            405             410             415
Tyr Asn Lys Xaa Xaa Xaa Lys Xaa Xaa Pro Glu Arg Xaa Xaa Gly Xaa
            420             425             430
Xaa Trp Xaa Xaa Gln Xaa Xaa Xaa Leu Tyr Xaa Ile Lys Xaa Xaa Lys
            435             440             445
Met Xaa Xaa Xaa Pro Xaa Xaa Ser Glu Xaa Xaa Glu
        450             455             460

<210> SEQ ID NO 5
<211> LENGTH: 215
<212> TYPE: PRT
<213> ORGANISM: Homo sapiens

<400> SEQUENCE: 5

Gly Ile Pro Ala Glu Cys Thr Thr Ile Tyr Asn Arg Gly Glu His Thr
1               5                   10                  15
```

```
Ser Gly Met Tyr Ala Ile Arg Pro Ser Asn Ser Gln Val Phe His Val
            20                  25                  30

Tyr Cys Asp Val Ile Ser Gly Ser Pro Trp Thr Leu Ile Gln His Arg
        35                  40                  45

Ile Asp Gly Ser Gln Asn Phe Asn Glu Thr Trp Glu Asn Tyr Lys Tyr
50                  55                  60

Gly Phe Gly Arg Leu Asp Gly Glu Phe Trp Leu Gly Leu Glu Lys Ile
65                  70                  75                  80

Tyr Ser Ile Val Lys Gln Ser Asn Tyr Val Leu Arg Ile Glu Leu Glu
                85                  90                  95

Asp Trp Lys Asp Asn Lys His Tyr Ile Glu Tyr Ser Phe Tyr Leu Gly
            100                 105                 110

Asn His Glu Thr Asn Tyr Thr Leu His Leu Val Ala Ile Thr Gly Asn
        115                 120                 125

Val Pro Asn Ala Ile Pro Glu Asn Lys Asp Leu Val Phe Ser Thr Trp
130                 135                 140

Asp His Lys Ala Lys Gly His Phe Asn Cys Pro Glu Gly Tyr Ser Gly
145                 150                 155                 160

Gly Trp Trp Trp His Asp Glu Cys Gly Glu Asn Asn Leu Asn Gly Lys
                165                 170                 175

Tyr Asn Lys Pro Arg Ala Lys Ser Lys Pro Glu Arg Arg Arg Gly Leu
            180                 185                 190

Ser Trp Lys Ser Gln Asn Gly Arg Leu Tyr Ser Ile Lys Ser Thr Lys
        195                 200                 205

Met Leu Ile His Pro Thr Asp
    210                 215

<210> SEQ ID NO 6
<211> LENGTH: 231
<212> TYPE: PRT
<213> ORGANISM: Homo sapiens

<400> SEQUENCE: 6

Thr Thr Pro Phe Leu Gln Leu Asn Glu Ile Arg Asn Val Lys His Asp
1               5                   10                  15

Gly Ile Pro Ala Glu Cys Thr Thr Ile Tyr Asn Arg Gly Glu His Thr
            20                  25                  30

Ser Gly Met Tyr Ala Ile Arg Pro Ser Asn Ser Gln Val Phe His Val
        35                  40                  45

Tyr Cys Asp Val Ile Ser Gly Ser Pro Trp Thr Leu Ile Gln His Arg
50                  55                  60

Ile Asp Gly Ser Gln Asn Phe Asn Glu Thr Trp Glu Asn Tyr Lys Tyr
65                  70                  75                  80

Gly Phe Gly Arg Leu Asp Gly Glu Phe Trp Leu Gly Leu Glu Lys Ile
                85                  90                  95

Tyr Ser Ile Val Lys Gln Ser Asn Tyr Val Leu Arg Ile Glu Leu Glu
            100                 105                 110

Asp Trp Lys Asp Asn Lys His Tyr Ile Glu Tyr Ser Phe Tyr Leu Gly
        115                 120                 125

Asn His Glu Thr Asn Tyr Thr Leu His Leu Val Ala Ile Thr Gly Asn
130                 135                 140

Val Pro Asn Ala Ile Pro Glu Asn Lys Asp Leu Val Phe Ser Thr Trp
145                 150                 155                 160

Asp His Lys Ala Lys Gly His Phe Asn Cys Pro Glu Gly Tyr Ser Gly
                165                 170                 175
```

```
Gly Trp Trp Trp His Asp Glu Cys Gly Glu Asn Asn Leu Asn Gly Lys
            180                 185                 190

Tyr Asn Lys Pro Arg Ala Lys Ser Lys Pro Glu Arg Arg Gly Leu
        195                 200                 205

Ser Trp Lys Ser Gln Asn Gly Arg Leu Tyr Ser Ile Lys Ser Thr Lys
210                 215                 220

Met Leu Ile His Pro Thr Asp
225                 230

<210> SEQ ID NO 7
<211> LENGTH: 248
<212> TYPE: PRT
<213> ORGANISM: Homo sapiens

<400> SEQUENCE: 7

Ile Gln Glu Pro Thr Glu Ile Ser Leu Ser Ser Lys Pro Arg Ala Pro
1               5                   10                  15

Arg Thr Thr Pro Phe Leu Gln Leu Asn Glu Ile Arg Asn Val Lys His
                20                  25                  30

Asp Gly Ile Pro Ala Glu Cys Thr Thr Ile Tyr Asn Arg Gly Glu His
            35                  40                  45

Thr Ser Gly Met Tyr Ala Ile Arg Pro Ser Asn Ser Gln Val Phe His
    50                  55                  60

Val Tyr Cys Asp Val Ile Ser Gly Ser Pro Trp Thr Leu Ile Gln His
65                  70                  75                  80

Arg Ile Asp Gly Ser Gln Asn Phe Asn Glu Thr Trp Glu Asn Tyr Lys
                85                  90                  95

Tyr Gly Phe Gly Arg Leu Asp Gly Glu Phe Trp Leu Gly Leu Glu Lys
            100                 105                 110

Ile Tyr Ser Ile Val Lys Gln Ser Asn Tyr Val Leu Arg Ile Glu Leu
        115                 120                 125

Glu Asp Trp Lys Asp Asn Lys His Tyr Ile Glu Tyr Ser Phe Tyr Leu
    130                 135                 140

Gly Asn His Glu Thr Asn Tyr Thr Leu His Leu Val Ala Ile Thr Gly
145                 150                 155                 160

Asn Val Pro Asn Ala Ile Pro Glu Asn Lys Asp Leu Val Phe Ser Thr
                165                 170                 175

Trp Asp His Lys Ala Lys Gly His Phe Asn Cys Pro Glu Gly Tyr Ser
            180                 185                 190

Gly Gly Trp Trp Trp His Asp Glu Cys Gly Glu Asn Asn Leu Asn Gly
        195                 200                 205

Lys Tyr Asn Lys Pro Arg Ala Lys Ser Lys Pro Glu Arg Arg Arg Gly
    210                 215                 220

Leu Ser Trp Lys Ser Gln Asn Gly Arg Leu Tyr Ser Ile Lys Ser Thr
225                 230                 235                 240

Lys Met Leu Ile His Pro Thr Asp
                245

<210> SEQ ID NO 8
<211> LENGTH: 460
<212> TYPE: PRT
<213> ORGANISM: Homo sapiens

<400> SEQUENCE: 8

Met Phe Thr Ile Lys Leu Leu Leu Phe Ile Val Pro Leu Val Ile Ser
1               5                   10                  15
```

```
Ser Arg Ile Asp Gln Asp Asn Ser Ser Phe Asp Ser Leu Ser Pro Glu
            20                  25                  30

Pro Lys Ser Arg Phe Ala Met Leu Asp Asp Val Lys Ile Leu Ala Asn
        35                  40                  45

Gly Leu Leu Gln Leu Gly His Gly Leu Lys Asp Phe Val His Lys Thr
    50                  55                  60

Lys Gly Gln Ile Asn Asp Ile Phe Gln Lys Leu Asn Ile Phe Asp Gln
65                  70                  75                  80

Ser Phe Tyr Asp Leu Ser Leu Gln Thr Ser Glu Ile Lys Glu Glu Glu
                85                  90                  95

Lys Glu Leu Arg Arg Thr Thr Tyr Lys Leu Gln Val Lys Asn Glu Glu
            100                 105                 110

Val Lys Asn Met Ser Leu Glu Leu Asn Ser Lys Leu Glu Ser Leu Leu
        115                 120                 125

Glu Glu Lys Ile Leu Leu Gln Gln Lys Val Lys Tyr Leu Glu Glu Gln
    130                 135                 140

Leu Thr Asn Leu Ile Gln Asn Gln Pro Glu Thr Pro Glu His Pro Glu
145                 150                 155                 160

Val Thr Ser Leu Lys Thr Phe Val Glu Lys Gln Asp Asn Ser Ile Lys
                165                 170                 175

Asp Leu Leu Gln Thr Val Glu Asp Gln Tyr Lys Gln Leu Asn Gln Gln
            180                 185                 190

His Ser Gln Ile Lys Glu Ile Glu Asn Gln Leu Arg Arg Thr Ser Ile
        195                 200                 205

Gln Glu Pro Thr Glu Ile Ser Leu Ser Ser Lys Pro Arg Ala Pro Arg
    210                 215                 220

Thr Thr Pro Phe Leu Gln Leu Asn Glu Ile Arg Asn Val Lys His Asp
225                 230                 235                 240

Gly Ile Pro Ala Glu Cys Thr Thr Ile Tyr Asn Arg Gly Glu His Thr
                245                 250                 255

Ser Gly Met Tyr Ala Ile Arg Pro Ser Asn Ser Gln Val Phe His Val
            260                 265                 270

Tyr Cys Asp Val Ile Ser Gly Ser Pro Trp Thr Leu Ile Gln His Arg
        275                 280                 285

Ile Asp Gly Ser Gln Asn Phe Asn Glu Thr Trp Glu Asn Tyr Lys Tyr
    290                 295                 300

Gly Phe Gly Arg Leu Asp Gly Glu Phe Trp Leu Gly Leu Glu Lys Ile
305                 310                 315                 320

Tyr Ser Ile Val Lys Gln Ser Asn Tyr Val Leu Arg Ile Glu Leu Glu
                325                 330                 335

Asp Trp Lys Asp Asn Lys His Tyr Ile Glu Tyr Ser Phe Tyr Leu Gly
            340                 345                 350

Asn His Glu Thr Asn Tyr Thr Leu His Leu Val Ala Ile Thr Gly Asn
        355                 360                 365

Val Pro Asn Ala Ile Pro Glu Asn Lys Asp Leu Val Phe Ser Thr Trp
    370                 375                 380

Asp His Lys Ala Lys Gly His Phe Asn Cys Pro Glu Gly Tyr Ser Gly
385                 390                 395                 400

Gly Trp Trp Trp His Asp Glu Cys Gly Glu Asn Asn Leu Asn Gly Lys
                405                 410                 415

Tyr Asn Lys Pro Arg Ala Lys Ser Lys Pro Glu Arg Arg Arg Gly Leu
            420                 425                 430
```

Ser Trp Lys Ser Gln Asn Gly Arg Leu Tyr Ser Ile Lys Ser Thr Lys
    435                 440                 445

Met Leu Ile His Pro Thr Asp Ser Glu Ser Phe Glu
    450                 455                 460

<210> SEQ ID NO 9
<211> LENGTH: 215
<212> TYPE: PRT
<213> ORGANISM: Mus musculus

<400> SEQUENCE: 9

Asp Leu Pro Ala Asp Cys Ser Ala Val Tyr Asn Arg Gly Glu His Thr
1               5                   10                  15

Ser Gly Val Tyr Thr Ile Lys Pro Arg Asn Ser Gln Gly Phe Asn Val
            20                  25                  30

Tyr Cys Asp Thr Gln Ser Gly Ser Pro Trp Thr Leu Ile Gln His Arg
        35                  40                  45

Lys Asp Gly Ser Gln Asp Phe Asn Glu Thr Trp Glu Asn Tyr Glu Lys
    50                  55                  60

Gly Phe Gly Arg Leu Asp Gly Glu Phe Trp Leu Gly Leu Glu Lys Ile
65                  70                  75                  80

Tyr Ala Ile Val Gln Gln Ser Asn Tyr Ile Leu Arg Leu Glu Leu Gln
                85                  90                  95

Asp Trp Lys Asp Ser Lys His Tyr Val Glu Tyr Ser Phe His Leu Gly
            100                 105                 110

Ser His Glu Thr Asn Tyr Thr Leu His Val Ala Glu Ile Ala Gly Asn
        115                 120                 125

Ile Pro Gly Ala Leu Pro Glu His Thr Asp Leu Met Phe Ser Thr Trp
    130                 135                 140

Asn His Arg Ala Lys Gly Gln Leu Tyr Cys Pro Glu Ser Tyr Ser Gly
145                 150                 155                 160

Gly Trp Trp Trp Asn Asp Ile Cys Gly Glu Asn Asn Leu Asn Gly Lys
                165                 170                 175

Tyr Asn Lys Pro Arg Thr Lys Ser Arg Pro Glu Arg Arg Arg Gly Ile
            180                 185                 190

Tyr Trp Arg Pro Gln Ser Arg Lys Leu Tyr Ala Ile Lys Ser Ser Lys
        195                 200                 205

Met Met Leu Gln Pro Thr Thr
    210                 215

<210> SEQ ID NO 10
<211> LENGTH: 231
<212> TYPE: PRT
<213> ORGANISM: Mus musculus

<400> SEQUENCE: 10

Thr Thr Pro Pro Leu Gln Leu Asn Glu Thr Glu Asn Thr Glu Gln Asp
1               5                   10                  15

Asp Leu Pro Ala Asp Cys Ser Ala Val Tyr Asn Arg Gly Glu His Thr
            20                  25                  30

Ser Gly Val Tyr Thr Ile Lys Pro Arg Asn Ser Gln Gly Phe Asn Val
        35                  40                  45

Tyr Cys Asp Thr Gln Ser Gly Ser Pro Trp Thr Leu Ile Gln His Arg
    50                  55                  60

Lys Asp Gly Ser Gln Asp Phe Asn Glu Thr Trp Glu Asn Tyr Glu Lys
65                  70                  75                  80

```
Gly Phe Gly Arg Leu Asp Gly Glu Phe Trp Leu Gly Leu Glu Lys Ile
            85                  90                  95

Tyr Ala Ile Val Gln Gln Ser Asn Tyr Ile Leu Arg Leu Glu Leu Gln
            100                 105                 110

Asp Trp Lys Asp Ser Lys His Tyr Val Glu Tyr Ser Phe His Leu Gly
            115                 120                 125

Ser His Glu Thr Asn Tyr Thr Leu His Val Ala Glu Ile Ala Gly Asn
        130                 135                 140

Ile Pro Gly Ala Leu Pro Glu His Thr Asp Leu Met Phe Ser Thr Trp
145                 150                 155                 160

Asn His Arg Ala Lys Gly Gln Leu Tyr Cys Pro Glu Ser Tyr Ser Gly
                165                 170                 175

Gly Trp Trp Trp Asn Asp Ile Cys Gly Glu Asn Asn Leu Asn Gly Lys
            180                 185                 190

Tyr Asn Lys Pro Arg Thr Lys Ser Arg Pro Glu Arg Arg Gly Ile
            195                 200                 205

Tyr Trp Arg Pro Gln Ser Arg Lys Leu Tyr Ala Ile Lys Ser Ser Lys
210                 215                 220

Met Met Leu Gln Pro Thr Thr
225                 230

<210> SEQ ID NO 11
<211> LENGTH: 248
<212> TYPE: PRT
<213> ORGANISM: Mus musculus

<400> SEQUENCE: 11

Ile Gln Glu Pro Ser Glu Asn Ser Leu Ser Ser Lys Ser Arg Ala Pro
1               5                   10                  15

Arg Thr Thr Pro Pro Leu Gln Leu Asn Glu Thr Glu Asn Thr Glu Gln
            20                  25                  30

Asp Asp Leu Pro Ala Asp Cys Ser Ala Val Tyr Asn Arg Gly Glu His
        35                  40                  45

Thr Ser Gly Val Tyr Thr Ile Lys Pro Arg Asn Ser Gln Gly Phe Asn
    50                  55                  60

Val Tyr Cys Asp Thr Gln Ser Gly Ser Pro Trp Thr Leu Ile Gln His
65                  70                  75                  80

Arg Lys Asp Gly Ser Gln Asp Phe Asn Glu Thr Trp Glu Asn Tyr Glu
                85                  90                  95

Lys Gly Phe Gly Arg Leu Asp Gly Glu Phe Trp Leu Gly Leu Glu Lys
            100                 105                 110

Ile Tyr Ala Ile Val Gln Gln Ser Asn Tyr Ile Leu Arg Leu Glu Leu
            115                 120                 125

Gln Asp Trp Lys Asp Ser Lys His Tyr Val Glu Tyr Ser Phe His Leu
        130                 135                 140

Gly Ser His Glu Thr Asn Tyr Thr Leu His Val Ala Glu Ile Ala Gly
145                 150                 155                 160

Asn Ile Pro Gly Ala Leu Pro Glu His Thr Asp Leu Met Phe Ser Thr
                165                 170                 175

Trp Asn His Arg Ala Lys Gly Gln Leu Tyr Cys Pro Glu Ser Tyr Ser
            180                 185                 190

Gly Gly Trp Trp Trp Asn Asp Ile Cys Gly Glu Asn Asn Leu Asn Gly
        195                 200                 205

Lys Tyr Asn Lys Pro Arg Thr Lys Ser Arg Pro Glu Arg Arg Arg Gly
    210                 215                 220
```

```
Ile Tyr Trp Arg Pro Gln Ser Arg Lys Leu Tyr Ala Ile Lys Ser Ser
225                 230                 235                 240

Lys Met Met Leu Gln Pro Thr Thr
                245

<210> SEQ ID NO 12
<211> LENGTH: 455
<212> TYPE: PRT
<213> ORGANISM: Mus musculus

<400> SEQUENCE: 12

Met His Thr Ile Lys Leu Phe Leu Phe Val Val Pro Leu Val Ile Ala
1               5                   10                  15

Ser Arg Val Asp Pro Asp Leu Ser Ser Phe Asp Ser Ala Pro Ser Glu
            20                  25                  30

Pro Lys Ser Arg Phe Ala Met Leu Asp Asp Val Lys Ile Leu Ala Asn
        35                  40                  45

Gly Leu Leu Gln Leu Gly His Gly Leu Lys Asp Phe Val His Lys Thr
50                  55                  60

Lys Gly Gln Ile Asn Asp Ile Phe Gln Lys Leu Asn Ile Phe Asp Gln
65                  70                  75                  80

Ser Phe Tyr Asp Leu Ser Leu Arg Thr Asn Glu Ile Lys Glu Glu Glu
                85                  90                  95

Lys Glu Leu Arg Arg Thr Thr Ser Thr Leu Gln Val Lys Asn Glu Glu
            100                 105                 110

Val Lys Asn Met Ser Val Glu Leu Asn Ser Lys Leu Glu Ser Leu Leu
        115                 120                 125

Glu Glu Lys Thr Ala Leu Gln His Lys Val Arg Ala Leu Glu Glu Gln
130                 135                 140

Leu Thr Asn Leu Ile Leu Ser Pro Ala Gly Ala Gln Glu His Pro Glu
145                 150                 155                 160

Val Thr Ser Leu Lys Ser Phe Val Glu Gln Gln Asp Asn Ser Ile Arg
                165                 170                 175

Glu Leu Leu Gln Ser Val Glu Glu Gln Tyr Lys Gln Leu Ser Gln Gln
            180                 185                 190

His Met Gln Ile Lys Glu Ile Glu Lys Gln Leu Arg Lys Thr Gly Ile
        195                 200                 205

Gln Glu Pro Ser Glu Asn Ser Leu Ser Ser Lys Ser Arg Ala Pro Arg
210                 215                 220

Thr Thr Pro Pro Leu Gln Leu Asn Glu Thr Glu Asn Thr Glu Gln Asp
225                 230                 235                 240

Asp Leu Pro Ala Asp Cys Ser Ala Val Tyr Asn Arg Gly Glu His Thr
                245                 250                 255

Ser Gly Val Tyr Thr Ile Lys Pro Arg Asn Ser Gln Gly Phe Asn Val
            260                 265                 270

Tyr Cys Asp Thr Gln Ser Gly Ser Pro Trp Thr Leu Ile Gln His Arg
        275                 280                 285

Lys Asp Gly Ser Gln Asp Phe Asn Glu Thr Trp Glu Asn Tyr Glu Lys
290                 295                 300

Gly Phe Gly Arg Leu Asp Gly Glu Phe Trp Leu Gly Leu Glu Lys Ile
305                 310                 315                 320

Tyr Ala Ile Val Gln Gln Ser Asn Tyr Ile Leu Arg Leu Glu Leu Gln
                325                 330                 335

Asp Trp Lys Asp Ser Lys His Tyr Val Glu Tyr Ser Phe His Leu Gly
```

```
                     340                 345                 350
Ser His Glu Thr Asn Tyr Thr Leu His Val Ala Glu Ile Ala Gly Asn
            355                 360                 365

Ile Pro Gly Ala Leu Pro Glu His Thr Asp Leu Met Phe Ser Thr Trp
        370                 375                 380

Asn His Arg Ala Lys Gly Gln Leu Tyr Cys Pro Glu Ser Tyr Ser Gly
385                 390                 395                 400

Gly Trp Trp Trp Asn Asp Ile Cys Gly Glu Asn Asn Leu Asn Gly Lys
                    405                 410                 415

Tyr Asn Lys Pro Arg Thr Lys Ser Arg Pro Glu Arg Arg Gly Ile
                420                 425                 430

Tyr Trp Arg Pro Gln Ser Arg Lys Leu Tyr Ala Ile Lys Ser Ser Lys
            435                 440                 445

Met Met Leu Gln Pro Thr Thr
        450                 455

<210> SEQ ID NO 13
<211> LENGTH: 214
<212> TYPE: PRT
<213> ORGANISM: Bos taurus

<400> SEQUENCE: 13

Asp Ile Pro Ala Asp Cys Thr Ile Ile Tyr Asn Gln Gly Lys His Thr
1               5                   10                  15

Ser Gly Ile Tyr Ser Ile Arg Pro Ser Asn Ser Gln Val Phe Asn Val
            20                  25                  30

Tyr Cys Asp Val Lys Ser Gly Ser Ser Trp Thr Leu Ile Gln His Arg
        35                  40                  45

Ile Asp Gly Ser Gln Asn Phe Asn Glu Thr Trp Glu Asn Tyr Lys Tyr
    50                  55                  60

Gly Phe Gly Arg Leu Asp Gly Glu Phe Trp Leu Gly Leu Glu Lys Ile
65                  70                  75                  80

Tyr Ser Ile Val Met Gln Ser Asn Tyr Ile Leu Arg Ile Glu Leu Glu
                85                  90                  95

Asp Trp Lys Asp Lys Tyr Tyr Thr Glu Tyr Ser Phe His Leu Gly Asp
            100                 105                 110

His Glu Thr Asn Tyr Thr Leu His Leu Ala Glu Ile Ser Gly Asn Gly
        115                 120                 125

Pro Lys Ala Phe Pro Glu His Lys Asp Leu Met Phe Ser Thr Trp Asp
    130                 135                 140

His Lys Ala Lys Gly His Phe Asn Cys Pro Glu Ser Asn Ser Gly Gly
145                 150                 155                 160

Trp Trp Tyr His Asp Val Cys Gly Glu Asn Asn Leu Asn Gly Lys Tyr
                165                 170                 175

Asn Lys Pro Lys Ala Lys Ala Lys Pro Glu Arg Lys Glu Gly Ile Cys
            180                 185                 190

Trp Lys Ser Gln Asp Gly Arg Leu Tyr Ser Ile Lys Ala Thr Lys Met
        195                 200                 205

Leu Ile His Pro Ser Asp
    210

<210> SEQ ID NO 14
<211> LENGTH: 230
<212> TYPE: PRT
<213> ORGANISM: Bos taurus
```

```
<400> SEQUENCE: 14

Thr Thr Pro Ser Phe His Ser Asn Glu Thr Lys Asn Val Glu His Asp
1               5                   10                  15

Asp Ile Pro Ala Asp Cys Thr Ile Ile Tyr Asn Gln Gly Lys His Thr
            20                  25                  30

Ser Gly Ile Tyr Ser Ile Arg Pro Ser Asn Ser Gln Val Phe Asn Val
        35                  40                  45

Tyr Cys Asp Val Lys Ser Gly Ser Ser Trp Thr Leu Ile Gln His Arg
    50                  55                  60

Ile Asp Gly Ser Gln Asn Phe Asn Glu Thr Trp Glu Asn Tyr Lys Tyr
65                  70                  75                  80

Gly Phe Gly Arg Leu Asp Gly Glu Phe Trp Leu Gly Leu Glu Lys Ile
                85                  90                  95

Tyr Ser Ile Val Met Gln Ser Asn Tyr Ile Leu Arg Ile Glu Leu Glu
            100                 105                 110

Asp Trp Lys Asp Lys Tyr Tyr Thr Glu Tyr Ser Phe His Leu Gly Asp
        115                 120                 125

His Glu Thr Asn Tyr Thr Leu His Leu Ala Glu Ile Ser Gly Asn Gly
    130                 135                 140

Pro Lys Ala Phe Pro Glu His Lys Asp Leu Met Phe Ser Thr Trp Asp
145                 150                 155                 160

His Lys Ala Lys Gly His Phe Asn Cys Pro Glu Ser Asn Ser Gly Gly
                165                 170                 175

Trp Trp Tyr His Asp Val Cys Gly Glu Asn Asn Leu Asn Gly Lys Tyr
            180                 185                 190

Asn Lys Pro Lys Ala Lys Ala Lys Pro Glu Arg Lys Glu Gly Ile Cys
        195                 200                 205

Trp Lys Ser Gln Asp Gly Arg Leu Tyr Ser Ile Lys Ala Thr Lys Met
    210                 215                 220

Leu Ile His Pro Ser Asp
225                 230

<210> SEQ ID NO 15
<211> LENGTH: 247
<212> TYPE: PRT
<213> ORGANISM: Bos taurus

<400> SEQUENCE: 15

Ile Lys Glu Ser Thr Glu Ile Ser Leu Ser Ser Lys Pro Arg Ala Pro
1               5                   10                  15

Arg Thr Thr Pro Ser Phe His Ser Asn Glu Thr Lys Asn Val Glu His
            20                  25                  30

Asp Asp Ile Pro Ala Asp Cys Thr Ile Ile Tyr Asn Gln Gly Lys His
        35                  40                  45

Thr Ser Gly Ile Tyr Ser Ile Arg Pro Ser Asn Ser Gln Val Phe Asn
    50                  55                  60

Val Tyr Cys Asp Val Lys Ser Gly Ser Ser Trp Thr Leu Ile Gln His
65                  70                  75                  80

Arg Ile Asp Gly Ser Gln Asn Phe Asn Glu Thr Trp Glu Asn Tyr Lys
                85                  90                  95

Tyr Gly Phe Gly Arg Leu Asp Gly Glu Phe Trp Leu Gly Leu Glu Lys
            100                 105                 110

Ile Tyr Ser Ile Val Met Gln Ser Asn Tyr Ile Leu Arg Ile Glu Leu
        115                 120                 125
```

```
Glu Asp Trp Lys Asp Lys Tyr Tyr Thr Glu Tyr Ser Phe His Leu Gly
130                 135                 140

Asp His Glu Thr Asn Tyr Thr Leu His Leu Ala Glu Ile Ser Gly Asn
145                 150                 155                 160

Gly Pro Lys Ala Phe Pro Glu His Lys Asp Leu Met Phe Ser Thr Trp
                165                 170                 175

Asp His Lys Ala Lys Gly His Phe Asn Cys Pro Glu Ser Asn Ser Gly
                180                 185                 190

Gly Trp Trp Tyr His Asp Val Cys Gly Glu Asn Asn Leu Asn Gly Lys
                195                 200                 205

Tyr Asn Lys Pro Lys Ala Lys Ala Lys Pro Glu Arg Lys Glu Gly Ile
210                 215                 220

Cys Trp Lys Ser Gln Asp Gly Arg Leu Tyr Ser Ile Lys Ala Thr Lys
225                 230                 235                 240

Met Leu Ile His Pro Ser Asp
                245

<210> SEQ ID NO 16
<211> LENGTH: 459
<212> TYPE: PRT
<213> ORGANISM: Bos taurus

<400> SEQUENCE: 16

Met Tyr Thr Ile Lys Leu Phe Leu Ile Ile Ala Pro Leu Val Ile Ser
1               5                   10                  15

Ser Arg Thr Asp Gln Asp Tyr Thr Ser Leu Asp Ser Ile Ser Pro Glu
                20                  25                  30

Pro Lys Ser Arg Phe Ala Met Leu Asp Asp Val Lys Ile Leu Ala Asn
            35                  40                  45

Gly Leu Leu Gln Leu Gly His Gly Leu Lys Asp Phe Val His Lys Thr
50                  55                  60

Lys Gly Gln Ile Asn Asp Ile Phe Gln Lys Leu Asn Ile Phe Asp Gln
65                  70                  75                  80

Ser Phe Tyr Asp Leu Ser Leu Gln Thr Asn Glu Ile Lys Glu Glu Glu
                85                  90                  95

Lys Glu Leu Arg Arg Ala Thr Ser Lys Leu Gln Val Lys Asn Glu Glu
            100                 105                 110

Val Lys Asn Met Ser Leu Glu Leu Asp Ser Lys Leu Glu Ser Leu Leu
            115                 120                 125

Glu Glu Lys Ile Leu Leu Gln Gln Lys Val Arg Tyr Leu Glu Asp Gln
130                 135                 140

Leu Thr Asp Leu Ile Lys Asn Gln Pro Gln Ile Gln Glu Tyr Leu Glu
145                 150                 155                 160

Val Thr Ser Leu Lys Thr Leu Val Glu Gln Gln Asp Asn Ser Ile Lys
                165                 170                 175

Asp Leu Leu Gln Ile Val Glu Glu Gln Tyr Arg Gln Leu Asn Gln Gln
                180                 185                 190

Gln Ser Gln Ile Lys Glu Ile Glu Asn Gln Leu Arg Arg Thr Gly Ile
            195                 200                 205

Lys Glu Ser Thr Glu Ile Ser Leu Ser Ser Lys Pro Arg Ala Pro Arg
210                 215                 220

Thr Thr Pro Ser Phe His Ser Asn Glu Thr Lys Asn Val Glu His Asp
225                 230                 235                 240

Asp Ile Pro Ala Asp Cys Thr Ile Ile Tyr Asn Gln Gly Lys His Thr
                245                 250                 255
```

```
Ser Gly Ile Tyr Ser Ile Arg Pro Ser Asn Ser Gln Val Phe Asn Val
            260                 265                 270

Tyr Cys Asp Val Lys Ser Gly Ser Ser Trp Thr Leu Ile Gln His Arg
        275                 280                 285

Ile Asp Gly Ser Gln Asn Phe Asn Glu Thr Trp Glu Asn Tyr Lys Tyr
    290                 295                 300

Gly Phe Gly Arg Leu Asp Gly Glu Phe Trp Leu Gly Leu Glu Lys Ile
305                 310                 315                 320

Tyr Ser Ile Val Met Gln Ser Asn Tyr Ile Leu Arg Ile Glu Leu Glu
                325                 330                 335

Asp Trp Lys Asp Lys Tyr Tyr Thr Glu Tyr Ser Phe His Leu Gly Asp
            340                 345                 350

His Glu Thr Asn Tyr Thr Leu His Leu Ala Glu Ile Ser Gly Asn Gly
        355                 360                 365

Pro Lys Ala Phe Pro Glu His Lys Asp Leu Met Phe Ser Thr Trp Asp
    370                 375                 380

His Lys Ala Lys Gly His Phe Asn Cys Pro Glu Ser Asn Ser Gly Gly
385                 390                 395                 400

Trp Trp Tyr His Asp Val Cys Gly Glu Asn Asn Leu Asn Gly Lys Tyr
                405                 410                 415

Asn Lys Pro Lys Ala Lys Ala Lys Pro Glu Arg Lys Glu Gly Ile Cys
            420                 425                 430

Trp Lys Ser Gln Asp Gly Arg Leu Tyr Ser Ile Lys Ala Thr Lys Met
        435                 440                 445

Leu Ile His Pro Ser Asp Ser Glu Asn Ser Glu
    450                 455

<210> SEQ ID NO 17
<211> LENGTH: 215
<212> TYPE: PRT
<213> ORGANISM: Canis lupus

<400> SEQUENCE: 17

Asp Ile Pro Ala Asn Cys Thr Thr Ile Tyr Asn Arg Gly Glu His Thr
1               5                   10                  15

Ser Gly Ile Tyr Ser Ile Arg Pro Ser Asn Ser Gln Val Phe Asn Val
            20                  25                  30

Tyr Cys Asp Val Lys Ser Gly Ser Ser Trp Thr Leu Ile Gln His Arg
        35                  40                  45

Ile Asp Gly Ser Gln Asn Phe Asn Glu Thr Trp Glu Asn Tyr Arg Tyr
    50                  55                  60

Gly Phe Gly Arg Leu Asp Gly Glu Phe Trp Leu Gly Leu Glu Lys Ile
65                  70                  75                  80

Tyr Ser Ile Val Lys Gln Ser Asn Tyr Ile Leu Arg Ile Glu Leu Glu
                85                  90                  95

Asp Trp Asn Asp Asn Lys His Tyr Ile Glu Tyr Phe Phe His Leu Gly
            100                 105                 110

Asn His Glu Thr Asn Tyr Thr Leu His Leu Val Glu Ile Thr Gly Asn
        115                 120                 125

Ile Leu Asn Ala Leu Pro Glu His Lys Asp Leu Val Phe Ser Thr Trp
    130                 135                 140

Asp His Lys Ala Lys Gly His Val Asn Cys Pro Glu Ser Tyr Ser Gly
145                 150                 155                 160

Gly Trp Trp Trp His Asn Val Cys Gly Glu Asn Asn Leu Asn Gly Lys
```

```
                165                 170                 175
Tyr Asn Lys Gln Arg Ala Lys Thr Lys Pro Glu Arg Arg Gly Leu
            180                 185                 190

Tyr Trp Lys Ser Gln Asn Gly Arg Leu Tyr Ser Ile Lys Ser Thr Lys
        195                 200                 205

Met Leu Ile His Pro Ile Asp
    210                 215

<210> SEQ ID NO 18
<211> LENGTH: 231
<212> TYPE: PRT
<213> ORGANISM: Canis lupus

<400> SEQUENCE: 18

Thr Thr Pro Phe Leu His Leu Asn Glu Thr Lys Asn Val Glu His Asn
1               5                   10                  15

Asp Ile Pro Ala Asn Cys Thr Thr Ile Tyr Asn Arg Gly Glu His Thr
            20                  25                  30

Ser Gly Ile Tyr Ser Ile Arg Pro Ser Asn Ser Gln Val Phe Asn Val
        35                  40                  45

Tyr Cys Asp Val Lys Ser Gly Ser Ser Trp Thr Leu Ile Gln His Arg
50                  55                  60

Ile Asp Gly Ser Gln Asn Phe Asn Glu Thr Trp Glu Asn Tyr Arg Tyr
65                  70                  75                  80

Gly Phe Gly Arg Leu Asp Gly Glu Phe Trp Leu Gly Leu Glu Lys Ile
                85                  90                  95

Tyr Ser Ile Val Lys Gln Ser Asn Tyr Ile Leu Arg Ile Glu Leu Glu
            100                 105                 110

Asp Trp Asn Asp Asn Lys His Tyr Ile Glu Tyr Phe Phe His Leu Gly
        115                 120                 125

Asn His Glu Thr Asn Tyr Thr Leu His Leu Val Glu Ile Thr Gly Asn
    130                 135                 140

Ile Leu Asn Ala Leu Pro Glu His Lys Asp Leu Val Phe Ser Thr Trp
145                 150                 155                 160

Asp His Lys Ala Lys Gly His Val Asn Cys Pro Glu Ser Tyr Ser Gly
                165                 170                 175

Gly Trp Trp Trp His Asn Val Cys Gly Glu Asn Asn Leu Asn Gly Lys
            180                 185                 190

Tyr Asn Lys Gln Arg Ala Lys Thr Lys Pro Glu Arg Arg Arg Gly Leu
        195                 200                 205

Tyr Trp Lys Ser Gln Asn Gly Arg Leu Tyr Ser Ile Lys Ser Thr Lys
    210                 215                 220

Met Leu Ile His Pro Ile Asp
225                 230

<210> SEQ ID NO 19
<211> LENGTH: 248
<212> TYPE: PRT
<213> ORGANISM: Canis lupus

<400> SEQUENCE: 19

Ile Gln Glu Ser Thr Glu Asn Ser Leu Ser Ser Lys Pro Arg Ala Pro
1               5                   10                  15

Arg Thr Thr Pro Phe Leu His Leu Asn Glu Thr Lys Asn Val Glu His
            20                  25                  30

Asn Asp Ile Pro Ala Asn Cys Thr Thr Ile Tyr Asn Arg Gly Glu His
```

```
            35                  40                  45
Thr Ser Gly Ile Tyr Ser Ile Arg Pro Ser Asn Ser Gln Val Phe Asn
 50                  55                  60

Val Tyr Cys Asp Val Lys Ser Gly Ser Ser Trp Thr Leu Ile Gln His
 65                  70                  75                  80

Arg Ile Asp Gly Ser Gln Asn Phe Asn Glu Thr Trp Glu Asn Tyr Arg
                     85                  90                  95

Tyr Gly Phe Gly Arg Leu Asp Gly Glu Phe Trp Leu Gly Leu Glu Lys
                100                 105                 110

Ile Tyr Ser Ile Val Lys Gln Ser Asn Tyr Ile Leu Arg Ile Glu Leu
            115                 120                 125

Glu Asp Trp Asn Asp Asn Lys His Tyr Ile Glu Tyr Phe Phe His Leu
130                 135                 140

Gly Asn His Glu Thr Asn Tyr Thr Leu His Leu Val Glu Ile Thr Gly
145                 150                 155                 160

Asn Ile Leu Asn Ala Leu Pro Glu His Lys Asp Leu Val Phe Ser Thr
                165                 170                 175

Trp Asp His Lys Ala Lys Gly His Val Asn Cys Pro Glu Ser Tyr Ser
            180                 185                 190

Gly Gly Trp Trp Trp His Asn Val Cys Gly Glu Asn Leu Asn Gly
            195                 200                 205

Lys Tyr Asn Lys Gln Arg Ala Lys Thr Lys Pro Glu Arg Arg Arg Gly
210                 215                 220

Leu Tyr Trp Lys Ser Gln Asn Gly Arg Leu Tyr Ser Ile Lys Ser Thr
225                 230                 235                 240

Lys Met Leu Ile His Pro Ile Asp
                245

<210> SEQ ID NO 20
<211> LENGTH: 459
<212> TYPE: PRT
<213> ORGANISM: Canis lupus

<400> SEQUENCE: 20

Met Tyr Thr Ile Lys Leu Phe Leu Phe Ile Ile Pro Leu Val Ile Ser
 1               5                  10                  15

Ser Lys Ile Asp Arg Asp Tyr Ser Ser Tyr Asp Ser Val Ser Pro Glu
                20                  25                  30

Pro Lys Ser Arg Phe Ala Met Leu Asp Asp Val Lys Ile Leu Ala Asn
            35                  40                  45

Gly Leu Leu Gln Leu Gly His Gly Leu Lys Asp Phe Val His Lys Thr
 50                  55                  60

Lys Gly Gln Ile Asn Asp Ile Phe Gln Lys Leu Asn Ile Phe Asp Gln
 65                  70                  75                  80

Ser Phe Tyr Asp Leu Ser Leu Gln Thr Asn Glu Ile Lys Glu Glu Glu
                85                  90                  95

Lys Glu Leu Arg Arg Thr Thr Ser Lys Leu Gln Val Lys Asn Glu Glu
                100                 105                 110

Val Lys Asn Met Ser Leu Glu Leu Asn Ser Lys Val Glu Ser Leu Leu
            115                 120                 125

Glu Glu Lys Ile Leu Leu Gln Gln Lys Val Arg Tyr Leu Glu Lys Gln
130                 135                 140

Leu Thr Ser Leu Ile Lys Asn Gln Pro Glu Ile Gln Glu His Pro Glu
145                 150                 155                 160
```

```
Val Thr Ser Leu Lys Thr Phe Val Glu Gln Gln Asp Asn Ser Ile Lys
            165                 170                 175

Asp Leu Leu Gln Thr Val Glu Glu Gln Tyr Arg Gln Leu Asn Gln Gln
        180                 185                 190

His Ser Gln Ile Lys Glu Ile Glu Asn Gln Leu Arg Asn Val Ile Gln
    195                 200                 205

Glu Ser Thr Glu Asn Ser Leu Ser Ser Lys Pro Arg Ala Pro Arg Thr
210                 215                 220

Thr Pro Phe Leu His Leu Asn Glu Thr Lys Asn Val Glu His Asn Asp
225                 230                 235                 240

Ile Pro Ala Asn Cys Thr Thr Ile Tyr Asn Arg Gly Glu His Thr Ser
                245                 250                 255

Gly Ile Tyr Ser Ile Arg Pro Ser Asn Ser Gln Val Phe Asn Val Tyr
            260                 265                 270

Cys Asp Val Lys Ser Gly Ser Ser Trp Thr Leu Ile Gln His Arg Ile
        275                 280                 285

Asp Gly Ser Gln Asn Phe Asn Glu Thr Trp Glu Asn Tyr Arg Tyr Gly
    290                 295                 300

Phe Gly Arg Leu Asp Gly Glu Phe Trp Leu Gly Leu Glu Lys Ile Tyr
305                 310                 315                 320

Ser Ile Val Lys Gln Ser Asn Tyr Ile Leu Arg Ile Glu Leu Glu Asp
                325                 330                 335

Trp Asn Asp Asn Lys His Tyr Ile Glu Tyr Phe Phe His Leu Gly Asn
            340                 345                 350

His Glu Thr Asn Tyr Thr Leu His Leu Val Glu Ile Thr Gly Asn Ile
        355                 360                 365

Leu Asn Ala Leu Pro Glu His Lys Asp Leu Val Phe Ser Thr Trp Asp
    370                 375                 380

His Lys Ala Lys Gly His Val Asn Cys Pro Glu Ser Tyr Ser Gly Gly
385                 390                 395                 400

Trp Trp Trp His Asn Val Cys Gly Glu Asn Leu Asn Gly Lys Tyr
                405                 410                 415

Asn Lys Gln Arg Ala Lys Thr Lys Pro Glu Arg Arg Arg Gly Leu Tyr
            420                 425                 430

Trp Lys Ser Gln Asn Gly Arg Leu Tyr Ser Ile Lys Ser Thr Lys Met
        435                 440                 445

Leu Ile His Pro Ile Asp Ser Glu Ser Ser Glu
    450                 455

<210> SEQ ID NO 21
<211> LENGTH: 215
<212> TYPE: PRT
<213> ORGANISM: Equus caballus

<400> SEQUENCE: 21

Asp Phe Pro Ala Asp Cys Thr Thr Ile Tyr Asn Arg Gly Glu His Thr
1               5                   10                  15

Ser Gly Ile Tyr Ser Ile Lys Pro Ser Asn Ser Gln Val Phe Asn Val
            20                  25                  30

Tyr Cys Asp Val Ile Ser Gly Ser Trp Ile Leu Ile Gln Arg Arg
        35                  40                  45

Ile Asp Gly Ser Gln Asn Phe Asn Glu Thr Trp Gln Asn Tyr Lys Tyr
    50                  55                  60

Gly Phe Gly Arg Leu Asp Phe Glu Phe Trp Leu Gly Leu Glu Lys Ile
65                  70                  75                  80
```

Tyr Ser Ile Val Lys Arg Ser Asn Tyr Ile Leu Arg Ile Glu Leu Glu
                85                  90                  95

Asp Trp Lys Asp Asn Lys His Thr Ile Glu Tyr Ser Phe His Leu Gly
            100                 105                 110

Asn His Glu Thr Asn Tyr Thr Leu His Leu Val Glu Ile Thr Gly Asn
        115                 120                 125

Val Pro Asn Ala Leu Pro Glu His Lys Asp Leu Val Phe Ser Thr Trp
130                 135                 140

Asp His Lys Ala Lys Gly Gln Leu Asn Cys Leu Glu Ser Tyr Ser Gly
145                 150                 155                 160

Gly Trp Trp Trp His Asp Val Cys Gly Gly Asp Asn Pro Asn Gly Lys
                165                 170                 175

Tyr Asn Lys Pro Arg Ser Lys Thr Lys Pro Glu Arg Arg Gly Ile
            180                 185                 190

Cys Trp Lys Ser Gln Asn Gly Arg Leu Tyr Thr Ile Lys Ser Thr Lys
        195                 200                 205

Met Leu Ile His Pro Ile Asp
    210                 215

<210> SEQ ID NO 22
<211> LENGTH: 231
<212> TYPE: PRT
<213> ORGANISM: Equus caballus

<400> SEQUENCE: 22

Thr Thr Pro Ser Phe His Leu Asn Glu Thr Lys Asp Val Glu His Asp
1               5                   10                  15

Asp Phe Pro Ala Asp Cys Thr Thr Ile Tyr Asn Arg Gly Glu His Thr
            20                  25                  30

Ser Gly Ile Tyr Ser Ile Lys Pro Ser Asn Ser Gln Val Phe Asn Val
        35                  40                  45

Tyr Cys Asp Val Ile Ser Gly Ser Ser Trp Ile Leu Ile Gln Arg Arg
    50                  55                  60

Ile Asp Gly Ser Gln Asn Phe Asn Glu Thr Trp Gln Asn Tyr Lys Tyr
65                  70                  75                  80

Gly Phe Gly Arg Leu Asp Phe Glu Phe Trp Leu Gly Leu Glu Lys Ile
                85                  90                  95

Tyr Ser Ile Val Lys Arg Ser Asn Tyr Ile Leu Arg Ile Glu Leu Glu
            100                 105                 110

Asp Trp Lys Asp Asn Lys His Thr Ile Glu Tyr Ser Phe His Leu Gly
        115                 120                 125

Asn His Glu Thr Asn Tyr Thr Leu His Leu Val Glu Ile Thr Gly Asn
    130                 135                 140

Val Pro Asn Ala Leu Pro Glu His Lys Asp Leu Val Phe Ser Thr Trp
145                 150                 155                 160

Asp His Lys Ala Lys Gly Gln Leu Asn Cys Leu Glu Ser Tyr Ser Gly
                165                 170                 175

Gly Trp Trp Trp His Asp Val Cys Gly Gly Asp Asn Pro Asn Gly Lys
            180                 185                 190

Tyr Asn Lys Pro Arg Ser Lys Thr Lys Pro Glu Arg Arg Gly Ile
        195                 200                 205

Cys Trp Lys Ser Gln Asn Gly Arg Leu Tyr Thr Ile Lys Ser Thr Lys
    210                 215                 220

Met Leu Ile His Pro Ile Asp

```
                    225                 230

<210> SEQ ID NO 23
<211> LENGTH: 248
<212> TYPE: PRT
<213> ORGANISM: Equus caballus

<400> SEQUENCE: 23

Ile Gln Glu Ser Thr Glu Asn Ser Leu Ser Ser Lys Pro Arg Ala Pro
1               5                   10                  15

Arg Thr Thr Pro Ser Phe His Leu Asn Glu Thr Lys Asp Val Glu His
            20                  25                  30

Asp Asp Phe Pro Ala Asp Cys Thr Thr Ile Tyr Asn Arg Gly Glu His
        35                  40                  45

Thr Ser Gly Ile Tyr Ser Ile Lys Pro Ser Asn Ser Gln Val Phe Asn
    50                  55                  60

Val Tyr Cys Asp Val Ile Ser Gly Ser Ser Trp Ile Leu Ile Gln Arg
65                  70                  75                  80

Arg Ile Asp Gly Ser Gln Asn Phe Asn Glu Thr Trp Gln Asn Tyr Lys
                85                  90                  95

Tyr Gly Phe Gly Arg Leu Asp Phe Glu Phe Trp Leu Gly Leu Glu Lys
            100                 105                 110

Ile Tyr Ser Ile Val Lys Arg Ser Asn Tyr Ile Leu Arg Ile Glu Leu
        115                 120                 125

Glu Asp Trp Lys Asp Asn Lys His Thr Ile Glu Tyr Ser Phe His Leu
    130                 135                 140

Gly Asn His Glu Thr Asn Tyr Thr Leu His Leu Val Glu Ile Thr Gly
145                 150                 155                 160

Asn Val Pro Asn Ala Leu Pro Glu His Lys Asp Leu Val Phe Ser Thr
                165                 170                 175

Trp Asp His Lys Ala Lys Gly Gln Leu Asn Cys Leu Glu Ser Tyr Ser
            180                 185                 190

Gly Gly Trp Trp Trp His Asp Val Cys Gly Gly Asp Asn Pro Asn Gly
        195                 200                 205

Lys Tyr Asn Lys Pro Arg Ser Lys Thr Lys Pro Glu Arg Arg Arg Gly
    210                 215                 220

Ile Cys Trp Lys Ser Gln Asn Gly Arg Leu Tyr Thr Ile Lys Ser Thr
225                 230                 235                 240

Lys Met Leu Ile His Pro Ile Asp
                245

<210> SEQ ID NO 24
<211> LENGTH: 469
<212> TYPE: PRT
<213> ORGANISM: Equus caballus

<400> SEQUENCE: 24

Met Tyr Thr Ile Lys Leu Phe Leu Val Ile Ala Pro Leu Val Ile Ser
1               5                   10                  15

Ser Arg Ile Asp Gln Asp Tyr Ser Ser Leu Asp Ser Ile Pro Pro Glu
            20                  25                  30

Pro Lys Ser Arg Phe Ala Met Leu Asp Asp Val Lys Ile Leu Ala Asn
        35                  40                  45

Gly Leu Leu Gln Leu Gly His Gly Leu Lys Asp Phe Val His Lys Thr
    50                  55                  60

Lys Gly Gln Ile Asn Asp Ile Phe Gln Lys Leu Asn Ile Phe Asp Gln
```

```
                65                  70                  75                  80
        Ser Phe Tyr Ala Leu Ser Leu Gln Thr Asn Glu Ile Lys Glu Glu
                            85                  90                  95

Lys Glu Leu Arg Arg Thr Thr Ser Lys Leu Gln Val Lys Asn Glu Glu
                            100                 105                 110

Val Lys Asn Met Ser Leu Glu Leu Asn Ser Lys Leu Glu Ser Leu Leu
                            115                 120                 125

Glu Glu Lys Ser Leu Leu Gln Gln Lys Val Lys Tyr Leu Glu Glu Gln
                    130                 135                 140

Leu Thr Lys Leu Ile Lys Asn Gln Pro Glu Ile Gln Glu His Pro Glu
        145                 150                 155                 160

Val Thr Ser Leu Lys Thr Phe Val Glu Gln Gln Asp Asn Ser Ile Lys
                            165                 170                 175

Asp Leu Leu Gln Thr Met Glu Glu Gln Tyr Arg Gln Leu Asn Gln Gln
                            180                 185                 190

His Ser Gln Ile Lys Glu Ile Glu Asn Gln Leu Arg Arg Thr Gly Ile
                    195                 200                 205

Gln Glu Ser Thr Glu Asn Ser Leu Ser Ser Lys Pro Arg Ala Pro Arg
                    210                 215                 220

Thr Thr Pro Ser Phe His Leu Asn Glu Thr Lys Asp Val Glu His Asp
        225                 230                 235                 240

Asp Phe Pro Ala Asp Cys Thr Thr Ile Tyr Asn Arg Gly Glu His Thr
                            245                 250                 255

Ser Gly Ile Tyr Ser Ile Lys Pro Ser Asn Ser Gln Val Phe Asn Val
                    260                 265                 270

Tyr Cys Asp Val Ile Ser Gly Ser Ser Trp Ile Leu Ile Gln Arg Arg
                275                 280                 285

Ile Asp Gly Ser Gln Asn Phe Asn Glu Thr Trp Gln Asn Tyr Lys Tyr
        290                 295                 300

Gly Phe Gly Arg Leu Asp Phe Glu Phe Trp Leu Gly Leu Glu Lys Ile
        305                 310                 315                 320

Tyr Ser Ile Val Lys Arg Ser Asn Tyr Ile Leu Arg Ile Glu Leu Glu
                            325                 330                 335

Asp Trp Lys Asp Asn Lys His Thr Ile Glu Tyr Ser Phe His Leu Gly
                    340                 345                 350

Asn His Glu Thr Asn Tyr Thr Leu His Leu Val Glu Ile Thr Gly Asn
                    355                 360                 365

Val Pro Asn Ala Leu Pro Glu His Lys Asp Leu Val Phe Ser Thr Trp
        370                 375                 380

Asp His Lys Ala Lys Gly Gln Leu Asn Cys Leu Glu Ser Tyr Ser Gly
        385                 390                 395                 400

Gly Trp Trp Trp His Asp Val Cys Gly Gly Asp Asn Pro Asn Gly Lys
                        405                 410                 415

Tyr Asn Lys Pro Arg Ser Lys Thr Lys Pro Glu Arg Arg Arg Gly Ile
                    420                 425                 430

Cys Trp Lys Ser Gln Asn Gly Arg Leu Tyr Thr Ile Lys Ser Thr Lys
                435                 440                 445

Met Leu Ile His Pro Ile Asp Ser Glu Ser Phe Glu Leu Arg Gln Ile
            450                 455                 460

Lys Lys Pro Met Asn
        465

<210> SEQ ID NO 25
```

-continued

```
<211> LENGTH: 215
<212> TYPE: PRT
<213> ORGANISM: Artificial Sequence
<220> FEATURE:
<223> OTHER INFORMATION: Consensus sequence of invariant amino acids
      between positions 241-455 of human, mouse, bovine, canine and
      equine native ANGPTL3
<220> FEATURE:
<221> NAME/KEY: misc_feature
<222> LOCATION: (1)..(215)
<223> OTHER INFORMATION: "X" = any amino acid

<400> SEQUENCE: 25

Xaa Xaa Pro Ala Xaa Cys Xaa Xaa Tyr Asn Xaa Gly Xaa His Thr
1               5                   10                  15

Ser Gly Xaa Tyr Xaa Ile Xaa Pro Xaa Asn Ser Gln Xaa Phe Xaa Val
            20                  25                  30

Tyr Cys Asp Xaa Xaa Ser Gly Ser Xaa Trp Xaa Leu Ile Gln Xaa Arg
        35                  40                  45

Xaa Asp Gly Ser Gln Xaa Phe Asn Glu Thr Trp Xaa Asn Tyr Xaa Xaa
    50                  55                  60

Gly Phe Gly Arg Leu Asp Xaa Glu Phe Trp Leu Gly Leu Glu Lys Ile
65                  70                  75                  80

Tyr Xaa Ile Val Xaa Xaa Ser Asn Tyr Xaa Leu Glu Xaa Glu Leu Xaa
                85                  90                  95

Asp Trp Xaa Asp Xaa Lys Xaa Xaa Xaa Glu Tyr Xaa Phe Xaa Leu Gly
            100                 105                 110

Xaa His Glu Thr Asn Tyr Thr Leu His Xaa Xaa Xaa Ile Xaa Gly Asn
        115                 120                 125

Xaa Xaa Xaa Ala Xaa Pro Glu Xaa Xaa Asp Leu Xaa Phe Ser Thr Trp
    130                 135                 140

Xaa His Xaa Ala Lys Gly Xaa Xaa Xaa Cys Xaa Glu Xaa Xaa Ser Gly
145                 150                 155                 160

Gly Trp Trp Xaa Xaa Xaa Xaa Cys Gly Xaa Xaa Asn Xaa Asn Gly Lys
                165                 170                 175

Tyr Asn Lys Xaa Xaa Xaa Lys Xaa Xaa Pro Glu Arg Xaa Xaa Gly Xaa
            180                 185                 190

Xaa Trp Xaa Xaa Gln Xaa Xaa Xaa Leu Tyr Xaa Ile Lys Xaa Xaa Lys
        195                 200                 205

Met Xaa Xaa Xaa Pro Xaa Xaa
    210                 215

<210> SEQ ID NO 26
<211> LENGTH: 231
<212> TYPE: PRT
<213> ORGANISM: Artificial Sequence
<220> FEATURE:
<223> OTHER INFORMATION: Consensus sequence of invariant amino acids
      between positions 225-455 of human, mouse, bovine, canine and
      equine ANGPTL3 proteins
<220> FEATURE:
<221> NAME/KEY: misc_feature
<222> LOCATION: (1)..(231)
<223> OTHER INFORMATION: "X" = any amino acid

<400> SEQUENCE: 26

Thr Thr Pro Xaa Xaa Xaa Xaa Asn Glu Xaa Xaa Xaa Xaa Xaa Xaa Xaa
1               5                   10                  15

Xaa Xaa Pro Ala Xaa Cys Xaa Xaa Xaa Tyr Asn Xaa Gly Xaa His Thr
            20                  25                  30

Ser Gly Xaa Tyr Xaa Ile Xaa Pro Xaa Asn Ser Gln Xaa Phe Xaa Val
```

```
            35                  40                  45
Tyr Cys Asp Xaa Xaa Ser Gly Ser Xaa Trp Xaa Leu Ile Gln Xaa Arg
 50                  55                  60

Xaa Asp Gly Ser Gln Xaa Phe Asn Glu Thr Trp Xaa Asn Tyr Xaa Xaa
 65                  70                  75                  80

Gly Phe Gly Arg Leu Asp Xaa Glu Phe Trp Leu Gly Leu Glu Lys Ile
                     85                  90                  95

Tyr Xaa Ile Val Xaa Xaa Ser Asn Tyr Xaa Leu Glu Xaa Glu Leu Xaa
                100                 105                 110

Asp Trp Xaa Asp Xaa Lys Xaa Xaa Xaa Glu Tyr Xaa Phe Xaa Leu Gly
            115                 120                 125

Xaa His Glu Thr Asn Tyr Thr Leu His Xaa Xaa Xaa Ile Xaa Gly Asn
130                 135                 140

Xaa Xaa Xaa Ala Xaa Pro Glu Xaa Xaa Asp Leu Xaa Phe Ser Thr Trp
145                 150                 155                 160

Xaa His Xaa Ala Lys Gly Xaa Xaa Xaa Cys Xaa Glu Xaa Xaa Ser Gly
                165                 170                 175

Gly Trp Trp Xaa Xaa Xaa Xaa Cys Gly Xaa Xaa Asn Xaa Asn Gly Lys
                180                 185                 190

Tyr Asn Lys Xaa Xaa Xaa Lys Xaa Xaa Pro Glu Arg Xaa Xaa Gly Xaa
                195                 200                 205

Xaa Trp Xaa Xaa Gln Xaa Xaa Xaa Leu Tyr Xaa Ile Lys Xaa Xaa Lys
            210                 215                 220

Met Xaa Xaa Xaa Pro Xaa Xaa
225                 230

<210> SEQ ID NO 27
<211> LENGTH: 249
<212> TYPE: PRT
<213> ORGANISM: Artificial Sequence
<220> FEATURE:
<223> OTHER INFORMATION: Consensus sequence of invariant amino acids in
      positions 207-455 of human, mouse, bovine and canine ANGPTL3
      proteins
<220> FEATURE:
<221> NAME/KEY: misc_feature
<222> LOCATION: (1)..(249)
<223> OTHER INFORMATION: "X" = any amino acid

<400> SEQUENCE: 27

Xaa Ile Xaa Glu Xaa Xaa Glu Xaa Ser Leu Ser Ser Lys Xaa Arg Ala
 1               5                  10                  15

Pro Arg Thr Thr Pro Xaa Xaa Xaa Asn Glu Xaa Xaa Xaa Xaa Xaa Xaa
                20                  25                  30

Xaa Xaa Xaa Xaa Pro Ala Xaa Cys Xaa Xaa Xaa Tyr Asn Xaa Gly Xaa
            35                  40                  45

His Thr Ser Gly Xaa Tyr Xaa Ile Xaa Pro Xaa Asn Ser Gln Xaa Phe
 50                  55                  60

Xaa Val Tyr Cys Asp Xaa Xaa Ser Gly Ser Xaa Trp Xaa Leu Ile Gln
 65                  70                  75                  80

Xaa Arg Xaa Asp Gly Ser Gln Xaa Phe Asn Glu Thr Trp Xaa Asn Tyr
                 85                  90                  95

Xaa Xaa Gly Phe Gly Arg Leu Asp Xaa Glu Phe Trp Leu Gly Leu Glu
                100                 105                 110

Lys Ile Tyr Xaa Ile Val Xaa Xaa Ser Asn Tyr Xaa Leu Glu Xaa Glu
            115                 120                 125

Leu Xaa Asp Trp Xaa Asp Xaa Lys Xaa Xaa Xaa Glu Tyr Xaa Phe Xaa
```

```
                130             135             140
Leu Gly Xaa His Glu Thr Asn Tyr Thr Leu His Xaa Xaa Xaa Ile Xaa
145             150             155             160

Gly Asn Xaa Xaa Xaa Ala Xaa Pro Glu Xaa Xaa Asp Leu Xaa Phe Ser
            165             170             175

Thr Trp Xaa His Xaa Ala Lys Gly Xaa Xaa Xaa Cys Xaa Glu Xaa Xaa
            180             185             190

Ser Gly Gly Trp Trp Xaa Xaa Xaa Cys Gly Xaa Xaa Asn Xaa Asn
            195             200             205

Gly Lys Tyr Asn Lys Xaa Xaa Xaa Lys Xaa Xaa Pro Glu Arg Xaa Xaa
            210             215             220

Gly Xaa Xaa Trp Xaa Xaa Gln Xaa Xaa Xaa Leu Tyr Xaa Ile Lys Xaa
225             230             235             240

Xaa Lys Met Xaa Xaa Xaa Pro Xaa Xaa
            245

<210> SEQ ID NO 28
<211> LENGTH: 469
<212> TYPE: PRT
<213> ORGANISM: Artificial Sequence
<220> FEATURE:
<223> OTHER INFORMATION: Consensus sequence of invariant amino acids for
      full-length human, bovine, mouse  and canine ANGPTL3 proteins
<220> FEATURE:
<221> NAME/KEY: misc_feature
<222> LOCATION: (1)..(469)
<223> OTHER INFORMATION: "X" = any amino acid

<400> SEQUENCE: 28

Met Xaa Thr Ile Lys Leu Xaa Leu Xaa Xaa Xaa Pro Leu Val Ile Xaa
1               5               10              15

Ser Xaa Xaa Asp Xaa Asp Xaa Xaa Ser Xaa Asp Ser Xaa Xaa Xaa Glu
            20              25              30

Pro Lys Ser Arg Phe Ala Met Leu Asp Asp Val Lys Ile Leu Ala Asn
            35              40              45

Gly Leu Leu Gln Leu Gly His Gly Leu Lys Asp Phe Val His Lys Thr
50              55              60

Lys Gly Gln Ile Asn Asp Ile Phe Gln Lys Leu Asn Ile Phe Asp Gln
65              70              75              80

Ser Phe Tyr Xaa Leu Ser Leu Xaa Thr Xaa Glu Ile Lys Glu Glu Glu
            85              90              95

Lys Glu Leu Arg Arg Xaa Thr Xaa Xaa Leu Gln Val Lys Asn Glu Glu
            100             105             110

Val Lys Asn Met Ser Xaa Glu Leu Xaa Ser Lys Xaa Glu Ser Leu Leu
            115             120             125

Glu Glu Lys Xaa Xaa Leu Gln Xaa Lys Val Xaa Xaa Leu Glu Xaa Gln
130             135             140

Leu Thr Xaa Leu Ile Xaa Xaa Xaa Xaa Xaa Xaa Glu Xaa Xaa Glu
145             150             155             160

Val Thr Ser Leu Lys Xaa Xaa Val Glu Xaa Gln Asp Asn Ser Ile Xaa
            165             170             175

Xaa Leu Leu Gln Xaa Xaa Glu Xaa Gln Tyr Gln Leu Xaa Gln Gln
            180             185             190

Xaa Xaa Gln Ile Lys Glu Ile Glu Xaa Gln Leu Arg Xaa Xaa Xaa Ile
            195             200             205

Xaa Glu Xaa Xaa Glu Xaa Ser Leu Ser Ser Lys Xaa Arg Ala Pro Arg
210             215             220
```

```
Thr Thr Pro Xaa Xaa Xaa Xaa Asn Glu Xaa Xaa Xaa Xaa Xaa Xaa
225                 230                 235                 240

Xaa Xaa Pro Ala Xaa Cys Xaa Xaa Xaa Tyr Asn Xaa Gly Xaa His Thr
            245                 250                 255

Ser Gly Xaa Tyr Xaa Ile Xaa Pro Xaa Asn Ser Gln Xaa Phe Xaa Val
        260                 265                 270

Tyr Cys Asp Xaa Xaa Ser Gly Ser Xaa Trp Xaa Leu Ile Gln Xaa Arg
        275                 280                 285

Xaa Asp Gly Ser Gln Xaa Phe Asn Glu Thr Trp Xaa Asn Tyr Xaa Xaa
    290                 295                 300

Gly Phe Gly Arg Leu Asp Xaa Glu Phe Trp Leu Gly Leu Glu Lys Ile
305                 310                 315                 320

Tyr Xaa Ile Val Xaa Xaa Ser Asn Tyr Xaa Leu Glu Xaa Glu Leu Xaa
            325                 330                 335

Asp Trp Xaa Asp Xaa Lys Xaa Xaa Xaa Glu Tyr Xaa Phe Xaa Leu Gly
        340                 345                 350

Xaa His Glu Thr Asn Tyr Thr Leu His Xaa Xaa Xaa Ile Xaa Gly Asn
    355                 360                 365

Xaa Xaa Xaa Ala Xaa Pro Glu Xaa Xaa Asp Leu Xaa Phe Ser Thr Trp
370                 375                 380

Xaa His Xaa Ala Lys Gly Xaa Xaa Xaa Cys Xaa Glu Xaa Xaa Ser Gly
385                 390                 395                 400

Gly Trp Trp Xaa Xaa Xaa Xaa Cys Gly Xaa Xaa Asn Xaa Asn Gly Lys
            405                 410                 415

Tyr Asn Lys Xaa Xaa Xaa Lys Xaa Xaa Pro Glu Arg Xaa Xaa Gly Xaa
            420                 425                 430

Xaa Trp Xaa Xaa Gln Xaa Xaa Xaa Leu Tyr Xaa Ile Lys Xaa Xaa Lys
        435                 440                 445

Met Xaa Xaa Xaa Pro Xaa Xaa Ser Glu Xaa Xaa Glu Xaa Xaa Xaa Xaa
    450                 455                 460

Xaa Xaa Xaa Xaa Xaa
465
```

The invention claimed is:

1. A pharmaceutical composition suitable for intra-articular delivery comprising a polypeptide consisting of an amino acid sequence as set forth in any one of SEQ ID NO:5, SEQ ID NO:6, or SEQ ID NO:7, wherein said polypeptide is PEGylated.

2. The pharmaceutical composition of claim 1, wherein the polypeptide has chondrogenic activity.

3. The pharmaceutical composition of claim 1, wherein the polypeptide has angiogenic activity.

4. The pharmaceutical composition of claim 1, wherein the polypeptide has reduced glycosylation relative to a naturally-occurring human Angiopoietin-like 3 (ANGPTL3).

5. The pharmaceutical composition of claim 1, further comprising an effective amount of the polypeptide.

6. The pharmaceutical composition of claim 1, further comprising a buffer.

7. The pharmaceutical composition of claim 1, wherein the pharmaceutical composition is provided in a unit-dose container.

8. The pharmaceutical composition of claim 1, wherein the pharmaceutical composition is provided in a multi-dose container.

9. The pharmaceutical composition of claim 1, wherein the pharmaceutical composition is an aqueous solution.

10. The pharmaceutical composition of claim 1, wherein the pharmaceutical composition is a sterile powder.

11. The pharmaceutical composition of claim 1, further comprising hyaluronic acid.

12. The pharmaceutical composition of claim 1, further comprising a preservative.

13. The pharmaceutical composition of claim 1, further comprising a stabilizer.

14. The pharmaceutical composition of claim 1, further comprising an antioxidant.

* * * * *